US012234278B2

(12) United States Patent
Nussenzweig et al.

(10) Patent No.: US 12,234,278 B2
(45) Date of Patent: Feb. 25, 2025

(54) COMBINATION OF BROADLY NEUTRALIZING HIV ANTIBODIES AND VIRAL INDUCERS

(71) Applicant: The Rockefeller University, New York, NY (US)

(72) Inventors: Michel Nussenzweig, New York, NY (US); Ariel Halper-Stromberg, New York, NY (US); Ching-Lan Lu, New York, NY (US)

(73) Assignee: The Rockefeller University, New York, NY (US)

( * ) Notice: Subject to any disclaimer, the term of this patent is extended or adjusted under 35 U.S.C. 154(b) by 546 days.

(21) Appl. No.: 16/885,797

(22) Filed: May 28, 2020

(65) Prior Publication Data

US 2020/0299365 A1   Sep. 24, 2020

Related U.S. Application Data

(62) Division of application No. 15/327,725, filed as application No. PCT/US2015/041272 on Jul. 21, 2015, now Pat. No. 10,676,521.

(60) Provisional application No. 62/026,915, filed on Jul. 21, 2014.

(51) Int. Cl.
| C07K 16/10 | (2006.01) |
| A61K 31/167 | (2006.01) |
| A61K 31/185 | (2006.01) |
| A61K 31/513 | (2006.01) |
| A61K 31/685 | (2006.01) |
| A61K 39/42 | (2006.01) |
| A61K 45/06 | (2006.01) |
| A61K 39/00 | (2006.01) |

(52) U.S. Cl.
CPC ........ *C07K 16/1063* (2013.01); *A61K 31/167* (2013.01); *A61K 31/185* (2013.01); *A61K 31/513* (2013.01); *A61K 31/685* (2013.01); *A61K 39/42* (2013.01); *A61K 45/06* (2013.01); *A61K 2039/505* (2013.01); *C07K 2317/33* (2013.01); *C07K 2317/52* (2013.01); *C07K 2317/71* (2013.01); *C07K 2317/76* (2013.01); *C07K 2317/94* (2013.01)

(58) Field of Classification Search
None
See application file for complete search history.

(56) References Cited

U.S. PATENT DOCUMENTS 5,855,887 A * 1/1999 Allison .................. A61K 39/39
424/139.1
2013/0189364 A1   7/2013 Sabin
2014/0017234 A1   1/2014 Diskin et al.
2014/0199260 A1   7/2014 Finkel et al.

FOREIGN PATENT DOCUMENTS

WO   WO-2012158948 A1 *  11/2012  ............. A61P 31/12

OTHER PUBLICATIONS

Klein, Florian, et al. "HIV therapy by a combination of broadly neutralizing antibodies in humanized mice." Nature 492.7427 (2012): 118-122 (Year: 2012).*
Pietzsch, John, et al. "A mouse model for HIV-1 entry." Proceedings of the National Academy of Sciences 109.39 (2012): 15859-15864 (Year: 2012).*
Boehm, Daniela et al. "BET bromodomain-targeting compounds reactivate HIV from latency via a Tat-independent mechanism." Cell cycle (Georgetown, Tex.) vol. 12,3 (2013): 452-62. doi:10.4161/cc.23309 (Year: 2013).*
Horwitz, Joshua A., et al. "HIV-1 suppression and durable control by combining single broadly neutralizing antibodies and antiretroviral drugs in humanized mice." Proceedings of the National Academy of Sciences 110.41 (2013): 16538-16543 (Year: 2013).*
Gallay, Philippe A., Christina M. Ramirez, and Marc M. Baum. "Acute antagonism in three-drug combinations for vaginal HIV prevention in humanized mice." Scientific Reports 13.1 (2023): 4594. (Year: 2023).*
Rathbun, R Chris, and Michelle D Liedtke. "Antiretroviral drug interactions: overview of interactions involving new and investigational agents and the role of therapeutic drug monitoring for management." Pharmaceutics vol. 3,4 745-81. Oct. 21, 2011, doi:10.3390/pharmaceutics3040745 (Year: 2011).*
Walker-Sperling, Victoria E., et al. "The effect of latency reversal agents on primary CD8+ T cells: implications for shock and kill strategies for human immunodeficiency virus eradication." EBioMedicine 8 (2016): 217-229. (Year: 2016).*
Caskey et al., "Broadly neutralizing anti-HIV-1 monoclonal antibodies in the clinic", Nature Medicine, vol. 25, 2019, pp. 547-553.
Dashti et al., "Broadly Neutralizing Antibodies against HIV: Back to Blood", Trends in Molecular Medicine, vol. 25, No. 3, 2019.
McCoy, "The expanding array of HIV broadly neutralizing antibodies", Retrovirology, 2018, 15:70.
Parsons et al., "Importance of Fc-mediated functions of anti-HIV-1 broadly neutralizing antibodies", Retrovirology, 2018, 15:58.
Possas et al., "HIV cure: global overview of bNAbs' patents and related scientific publications", Expert Opinion on Therapeutic Patents, 2018, vol. 28, No. 7, pp. 551-560.

(Continued)

*Primary Examiner* — Michael Szperka
*Assistant Examiner* — Lia E Taylor
(74) *Attorney, Agent, or Firm* — Fox Rothschild LLP

(57) ABSTRACT

The present invention relates to methods and agents for preventing the establishment of HIV-1 latent reservoirs or for reducing the size of the reservoirs. Specifically, the disclosure provides methods and agents for preventing the establishment of HIV-1 latent reservoirs or for reducing the size of the reservoirs, the methods comprising administering to the subject a therapeutically effective amount of an isolated anti-HIV antibody, and administering to the subject two or more viral transcription inducers in effective amounts to induce transcription of an HIV provirus in the cells. Further provided are antibodies and viral transcription inducers used in the methods.

1 Claim, 16 Drawing Sheets

Specification includes a Sequence Listing.

(56) References Cited

OTHER PUBLICATIONS

Sok et al., "Recent progress in broadly neutralizing antibodies to HIV", Nature Immunology, 2018, vol. 19, pp. 1179-1188.

Liu et al., "Broadly neutralizing antibodies for HIV-1: effecacies, challenges and opportunities", Emerging Microbes & Infections, 2020, vol. 9.

Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.

Pejchal et al., "Structure and function of broadly reactive antibody PG16 reveal an H3 subdomain that mediates potent neutralization of HIV-1," PNAS (Jun. 22, 2010); 107(25):11483-11488.

Li et al., "The BET bromodomain inhibitor JQ1 activates HIV latency through antagonizing Brd4 inhibition of Tat-transactivation," Nucleic Acids Research (2013): 41(1):277-287.

Cillo et al., "Quantification of HIV-1 latency reversal in resting CD4+ T cells from patients on suppressive antiretroviral therapy," PNAS (May 13, 2014); 111(19):7078-7083.

Horwitz et al., "HIV-1 suppression and durable control by combining single broadly neutralizing antibodies and antiretroviral drugs in humanized mice," PNAS (Oct. 8, 2013); 110(41):16538-16543.

Halper-Stromberg et al., "Broadly Neutralizing Antibodies and Viral Inducers Decrease Rebound From HIV-1 Latent Reservoirs in Humanized Mice," Cell (Aug. 28, 2014); 158:989-999.

Scripps_News_Release, "Two New Antibodies Found to Cripple HIV" The Scripps Research Institute (Sep. 3, 2009—online); pp. 1-6.

Ferrantelli et al., "Post-exposure prophylaxis with human monoclonal antibodies prevented SHIV89.6P infection or disease in neonatal macaques", AIDS, 2003; 17:301-309.

Shingai et al., "Antibody-mediated immunotherapy of macaques chronically infected with SHIV suppresses viraemia", Nature, 2013; 503: 277-281 and 10 pages of supplemental data (Year: 2013).

Deeks S. "Shock and Kill", Nature 2012; 487:439-440 (Year: 2012).

Klein et al., "HIV therapy by a combination of broadly neutralizing antibodies in humanized mice", Nature, 2012; 492(6): 118-122 plus two pages of Supplemental Content (Year: 2012).

\* cited by examiner

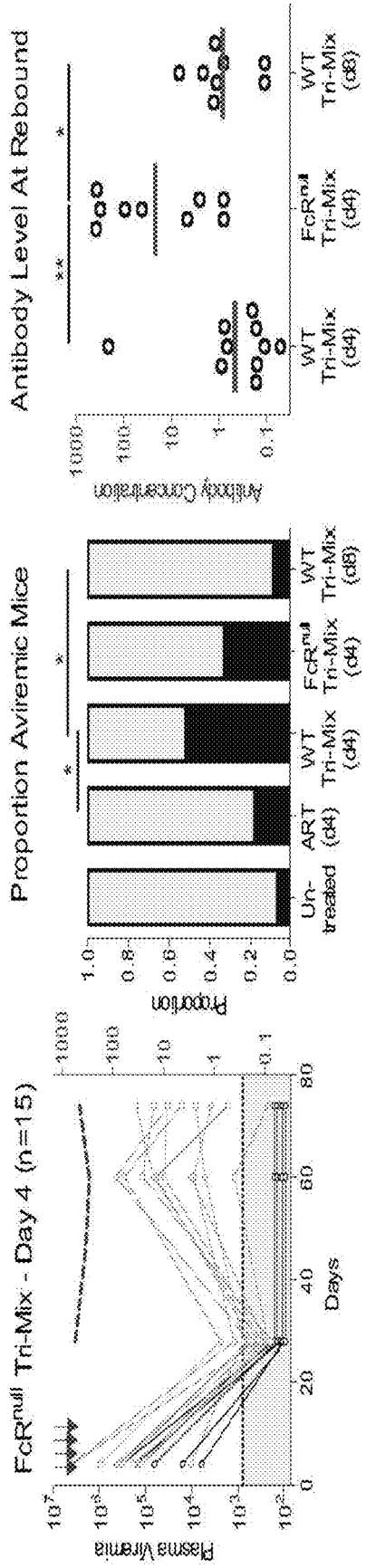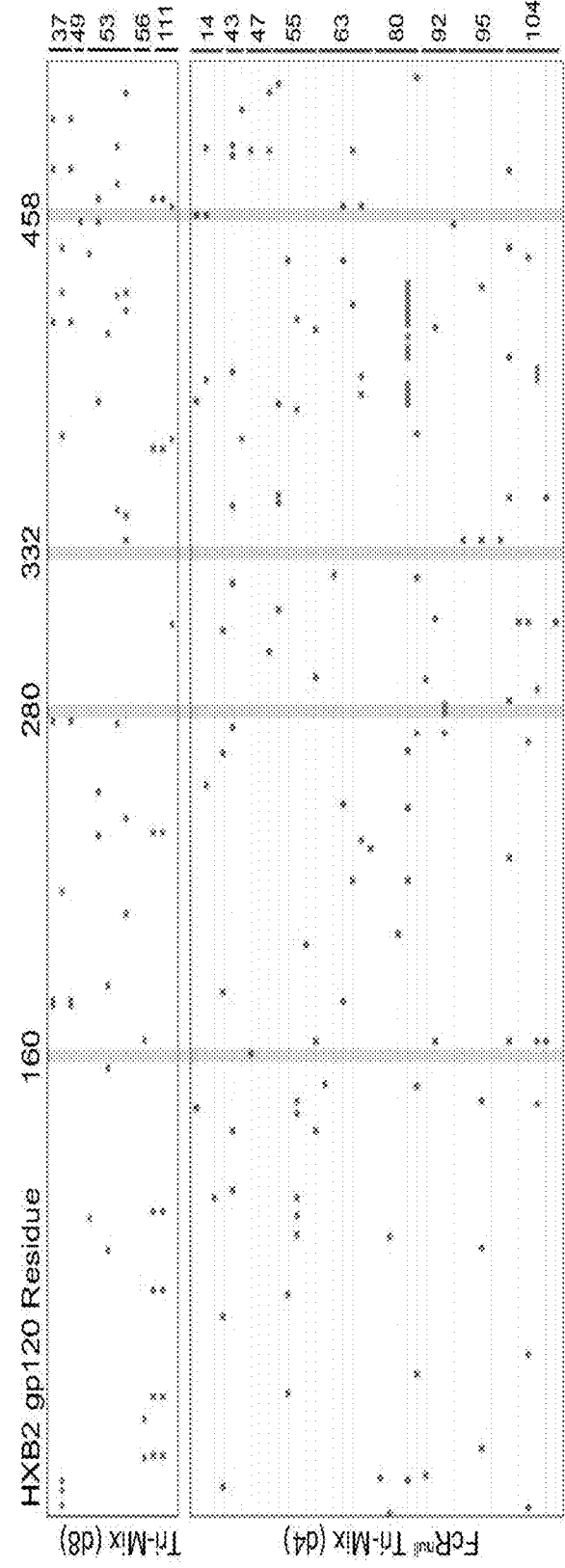
FIG. 2A
FIG. 2B
FIG. 2C
FIG. 2D

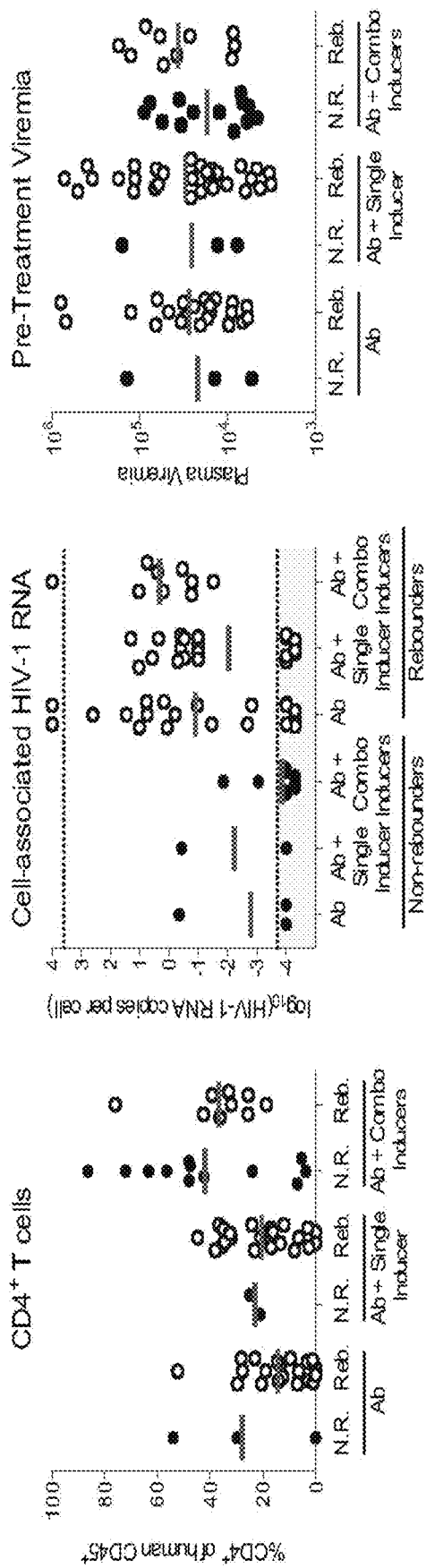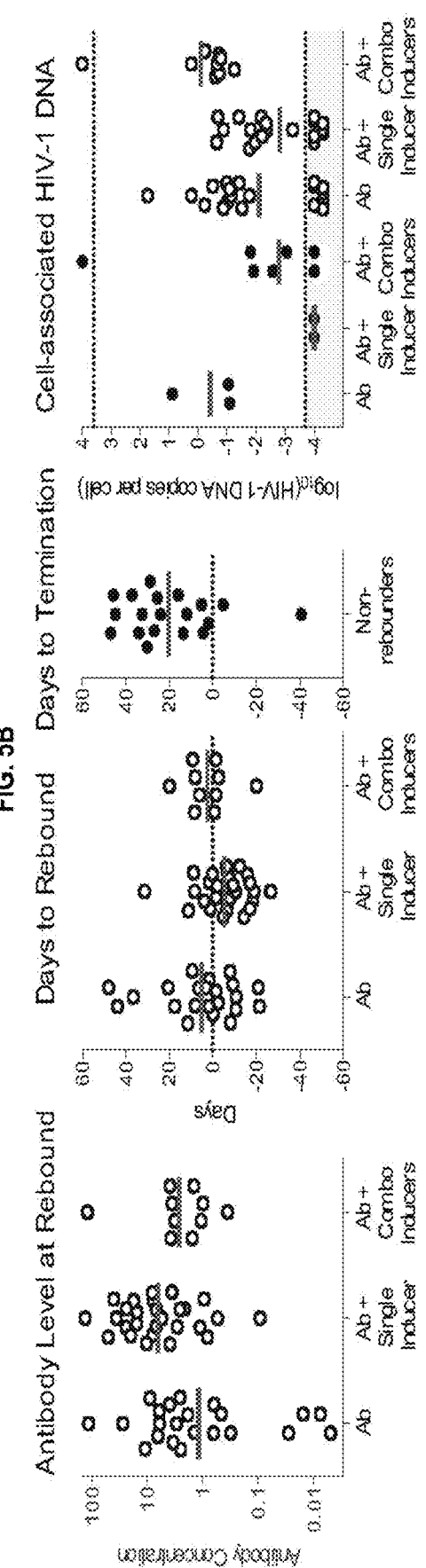

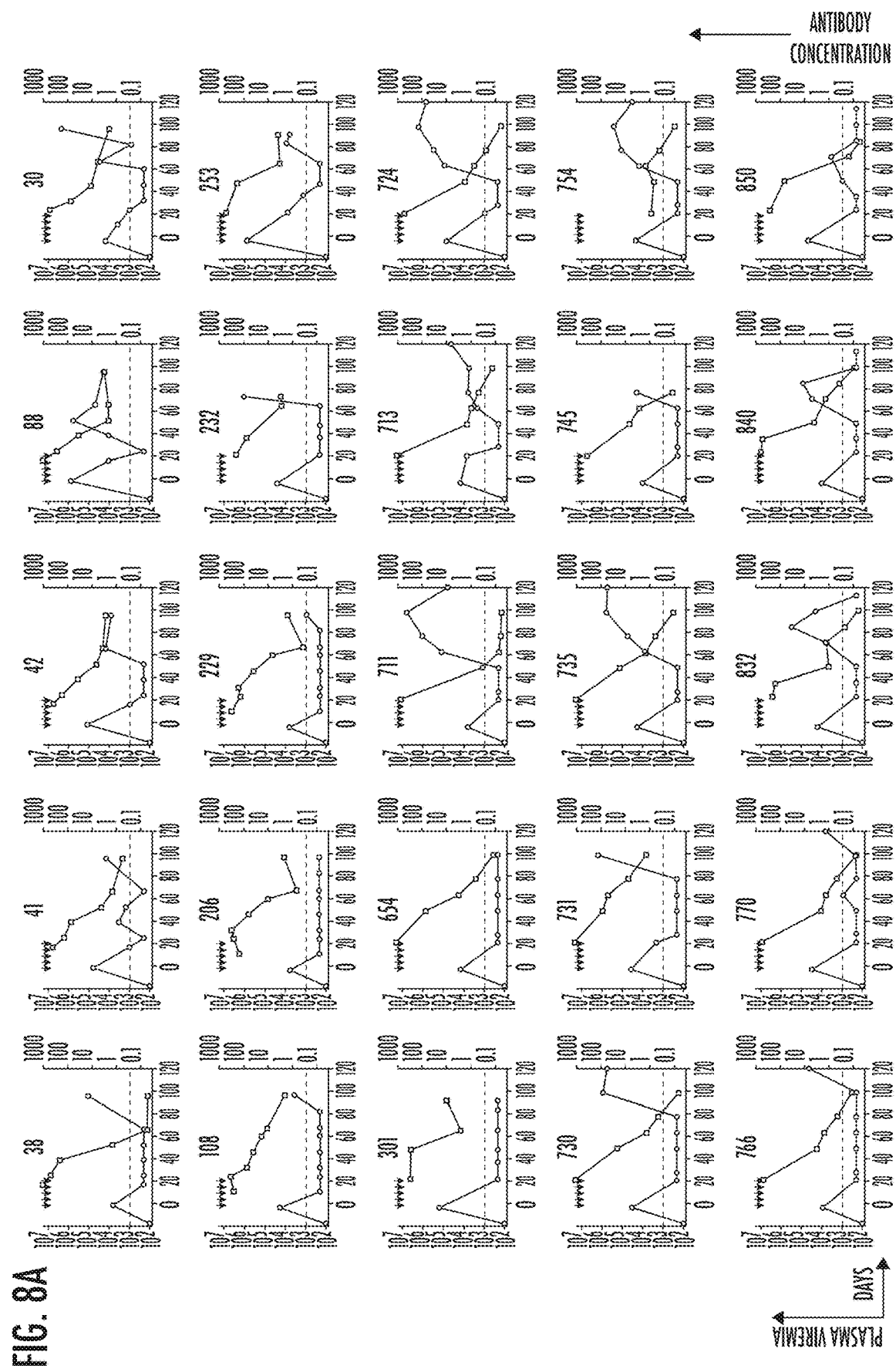

SEQUENCE LISTING

```
<160> NUMBER OF SEQ ID NOS: 55

<210> SEQ ID NO 1
<211> LENGTH: 128
<212> TYPE: PRT
<213> ORGANISM: Homo sapiens

<400> SEQUENCE: 1

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser Ala Ser Thr Lys Gly
        115                 120                 125

<210> SEQ ID NO 2
<211> LENGTH: 114
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
            35                  40                  45

Lys Leu Glu Arg Gly Val Pro Ser Arg Phe Ser Gly Arg Arg Trp Gly
        50                  55                  60

Gln Glu Tyr Asn Leu Thr Ile Asn Asn Leu Gln Pro Glu Asp Ile Ala
```

```
                65                  70                  75                  80
Thr Tyr Phe Cys Gln Val Tyr Glu Phe Val Pro Gly Thr Arg Leu
                    85                  90                  95

Asp Leu Lys Arg Thr Val Ala Ala Pro Ser Val Phe Ile Phe Pro Pro
                100                 105                 110

Ser Asp

<210> SEQ ID NO 3
<211> LENGTH: 128
<212> TYPE: PRT
<213> ORGANISM: Homo sapiens

<400> SEQUENCE: 3

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
        50                  55                  60

Gln Gly Arg Val Ser Leu Thr Arg Gln Ala Ser Trp Asp Phe Asp Thr
65                  70                  75                  80

Tyr Ser Phe Tyr Met Asp Leu Lys Ala Val Arg Ser Asp Asp Thr Ala
                85                  90                  95

Ile Tyr Phe Cys Ala Arg Gln Arg Ser Asp Phe Trp Asp Phe Asp Val
                100                 105                 110

Trp Gly Ser Gly Thr Gln Val Thr Val Ser Ser Ala Ser Thr Lys Gly
            115                 120                 125

<210> SEQ ID NO 4
<211> LENGTH: 104
<212> TYPE: PRT
<213> ORGANISM: Homo sapiens

<400> SEQUENCE: 4

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ala Arg Phe Ser Gly Arg Arg Trp Gly
        50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala Ala
                100

<210> SEQ ID NO 5
<211> LENGTH: 127
<212> TYPE: PRT
<213> ORGANISM: Homo sapiens

<400> SEQUENCE: 5
```

```
Ser Gln Gln Leu Val Gln Ser Gly Thr Gln Val Lys Lys Pro Gly Ala
1               5                   10                  15

Ser Val Arg Ile Ser Cys Gln Ala Ser Gly Tyr Ser Phe Thr Asp Tyr
            20                  25                  30

Val Leu His Trp Trp Arg Gln Ala Pro Gly Gln Gly Leu Glu Trp Met
        35                  40                  45

Gly Trp Ile Lys Pro Val Tyr Gly Ala Arg Asn Tyr Ala Arg Arg Phe
    50                  55                  60

Gln Gly Arg Ile Asn Phe Asp Arg Asp Ile Tyr Arg Glu Ile Ala Phe
65                  70                  75                  80

Met Asp Leu Ser Gly Leu Arg Ser Asp Asp Thr Ala Leu Tyr Phe Cys
            85                  90                  95

Ala Arg Asp Gly Ser Gly Asp Asp Thr Ser Trp His Leu Asp Pro Trp
            100                 105                 110

Gly Gln Gly Thr Leu Val Ile Val Ser Ala Ala Ser Thr Lys Gly
            115                 120                 125

<210> SEQ ID NO 6
<211> LENGTH: 123
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Gly Ile Gly Ser Ser
            20                  25                  30

Leu Gln Trp Tyr Gln Gln Lys Pro Gly Lys Ala Pro Lys Leu Leu Val
        35                  40                  45

His Gly Ala Ser Asn Leu His Arg Gly Val Pro Ser Arg Phe Ser Gly
    50                  55                  60

Ser Gly Phe His Thr Thr Phe Ser Leu Thr Ile Ser Gly Leu Gln Arg
65                  70                  75                  80

Asp Asp Phe Ala Thr Tyr Phe Cys Ala Val Leu Glu Phe Phe Gly Pro
            85                  90                  95

Gly Thr Lys Val Glu Ile Lys Arg Thr Val Ala Ala Pro Ser Val Phe
            100                 105                 110

Ile Phe Pro Pro Ser Asp Glu Gln Leu Lys Ser
            115                 120

<210> SEQ ID NO 7
<211> LENGTH: 127
<212> TYPE: PRT
<213> ORGANISM: Homo sapiens

<400> SEQUENCE: 7

Ser Gln His Leu Val Gln Ser Gly Thr Gln Val Lys Lys Pro Gly Ala
1               5                   10                  15

Ser Val Arg Val Ser Cys Gln Ala Ser Gly Tyr Thr Phe Thr Asn Tyr
            20                  25                  30

Ile Leu His Trp Trp Arg Gln Ala Pro Gly Gln Gly Leu Glu Trp Met
        35                  40                  45

Gly Leu Ile Lys Pro Val Phe Gly Ala Val Asn Tyr Ala Arg Gln Phe
    50                  55                  60

Gln Gly Arg Ile Gln Leu Thr Arg Asp Ile Tyr Arg Glu Ile Ala Phe
65                  70                  75                  80
```

Leu Asp Leu Ser Gly Leu Arg Ser Asp Asp Thr Ala Val Tyr Tyr Cys
            85                  90                  95

Ala Arg Asp Glu Ser Gly Asp Asp Leu Lys Trp His Leu His Pro Trp
            100                 105                 110

Gly Gln Gly Thr Gln Val Ile Val Ser Pro Ala Ser Thr Lys Gly
        115                 120                 125

<210> SEQ ID NO 8
<211> LENGTH: 122
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30

Leu Asn Trp Tyr Gln Lys Lys Pro Gly Arg Ala Pro Lys Leu Leu Val
        35                  40                  45

His Gly Ala Ser Asn Leu Gln Arg Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Val Ala Thr Tyr Phe Cys Ala Val Phe Gln Trp Phe Gly Pro
                85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys
        115                 120

<210> SEQ ID NO 9
<211> LENGTH: 114
<212> TYPE: PRT
<213> ORGANISM: Homo sapiens

<400> SEQUENCE: 9

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
        35                  40                  45

Gly Trp Leu Lys Pro Arg Gly Gly Ala Val Asn Tyr Ala Arg Lys Phe
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His

<210> SEQ ID NO 10
<211> LENGTH: 91
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Ser Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

Phe Gly Val Tyr Tyr Cys Gln Gln Tyr Glu Phe
            85                  90

<210> SEQ ID NO 11
<211> LENGTH: 129
<212> TYPE: PRT
<213> ORGANISM: Homo sapiens

<400> SEQUENCE: 11

Gln Gly Gln Leu Val Gln Ser Gly Gly Gly Leu Lys Lys Pro Gly Thr
1               5                   10                  15

Ser Val Thr Ile Ser Cys Leu Ala Ser Glu Tyr Thr Phe Asn Glu Phe
            20                  25                  30

Val Ile His Trp Ile Arg Gln Ala Pro Gly Gln Gly Pro Leu Trp Leu
        35                  40                  45

Gly Leu Ile Lys Arg Ser Gly Arg Leu Met Thr Ala Tyr Asn Phe Gln
    50                  55                  60

Asp Arg Leu Arg Leu Arg Arg Asp Arg Ser Thr Gly Thr Val Phe Met
65                  70                  75                  80

Glu Leu Arg Gly Leu Arg Pro Asp Asp Thr Ala Val Tyr Tyr Cys Ala
                85                  90                  95

Arg Asp Gly Leu Gly Glu Val Ala Pro Asp Tyr Arg Tyr Gly Ile Asp
            100                 105                 110

Val Trp Gly Gln Gly Ser Thr Val Ile Val Thr Ala Ala Ser Thr Lys
        115                 120                 125

Gly

<210> SEQ ID NO 12
<211> LENGTH: 123
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Asn Phe Val
            20                  25                  30

Val Trp Tyr Gln Gln Lys Arg Gly Gln Ala Pro Arg Leu Leu Ile His
        35                  40                  45

Ala Pro Ser Gly Arg Ala Pro Gly Val Pro Asp Arg Phe Ser Ala Arg
    50                  55                  60

Gly Ser Gly Thr Glu Phe Ser Leu Val Ile Ser Ser Val Glu Pro Asp
65                  70                  75                  80

Asp Phe Ala Ile Tyr Tyr Cys Gln Glu Tyr Ser Ser Thr Pro Tyr Asn
            85                  90                  95

```
Phe Gly Pro Gly Thr Arg Val Asp Arg Lys Arg Thr Val Ala Ala Pro
                100                 105                 110

Ser Val Phe Ile Phe Pro Pro Ser Asp Glu Gln
            115                 120
```

<210> SEQ ID NO 13
<211> LENGTH: 129
<212> TYPE: PRT
<213> ORGANISM: Homo sapiens

<400> SEQUENCE: 13

```
Gln Gly Gln Leu Val Gln Ser Gly Gly Val Lys Lys Pro Gly Thr
1               5                   10                  15

Ser Val Thr Ile Ser Cys Leu Ala Ser Glu Tyr Thr Phe Asn Glu Phe
                20                  25                  30

Val Ile His Trp Ile Arg Gln Ala Pro Gly Gln Gly Pro Val Trp Leu
                35                  40                  45

Gly Leu Ile Lys Arg Ser Gly Arg Leu Met Thr Ser Tyr Lys Phe Gln
            50                  55                  60

Asp Arg Leu Ser Leu Arg Arg Asp Arg Ser Thr Gly Thr Val Phe Met
65                  70                  75                  80

Glu Leu Arg Gly Leu Arg Leu Asp Asp Thr Ala Val Tyr Tyr Cys Ala
                85                  90                  95

Arg Asp Gly Leu Gly Glu Val Ala Pro Ala Tyr Leu Tyr Gly Ile Asp
                100                 105                 110

Ala Trp Gly Gln Gly Ser Thr Val Ile Val Thr Ser Ala Ser Thr Lys
            115                 120                 125

Gly
```

<210> SEQ ID NO 14
<211> LENGTH: 123
<212> TYPE: PRT
<213> ORGANISM: Homo sapiens

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Asn Phe Val
                20                  25                  30

Val Trp Tyr Gln Gln Lys Gly Gly Gln Ala Pro Arg Leu Leu Ile His
            35                  40                  45

Gly Pro Thr Asp Arg Ala Pro Gly Val Pro Asp Arg Phe Ser Ala Arg
        50                  55                  60

Gly Ser Gly Thr Glu Phe Ser Leu Val Ile Ser Ser Val Glu Pro Asp
65                  70                  75                  80

Asp Phe Ala Leu Tyr Tyr Cys Gln Glu Tyr Ser Ser Thr Pro Tyr Asn
                85                  90                  95

Phe Gly Pro Gly Thr Arg Val Asp Arg Lys Arg Thr Val Ala Ala Pro
                100                 105                 110

Ser Val Phe Ile Phe Pro Pro Ser Asp Glu Gln
            115                 120
```

<210> SEQ ID NO 15
<211> LENGTH: 114
<212> TYPE: PRT
<213> ORGANISM: Homo sapiens

<400> SEQUENCE: 15

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
    50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
            85                  90                  95

Ala Arg Ala Glu Ala Ala Ser Asp Ser His Ser Arg Pro Ile Met Phe
            100                 105                 110

Asp His

<210> SEQ ID NO 16
<211> LENGTH: 114
<212> TYPE: PRT
<213> ORGANISM: Homo sapiens

<400> SEQUENCE: 16

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
    50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
            85                  90                  95

Ala Arg Ala Glu Ala Ala Ser Asp Ser His Ser Arg Pro Ile Met Phe
            100                 105                 110

Asp His

<210> SEQ ID NO 17
<211> LENGTH: 114
<212> TYPE: PRT
<213> ORGANISM: Homo sapiens

<400> SEQUENCE: 17

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
    50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys

```
                85                  90                  95

Ala Arg Ala Glu Ala Ala Ser Asp Ser His Ser Arg Pro Ile Met Phe
            100                 105                 110

Asp His

<210> SEQ ID NO 18
<211> LENGTH: 114
<212> TYPE: PRT
<213> ORGANISM: Homo sapiens

<400> SEQUENCE: 18

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
                85                  90                  95

Ala Arg Ala Glu Ala Ala Ser Asp Ser His Ser Arg Pro Ile Met Phe
            100                 105                 110

Asp His

<210> SEQ ID NO 19
<211> LENGTH: 137
<212> TYPE: PRT
<213> ORGANISM: Homo sapiens

<400> SEQUENCE: 19

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly
    130                 135

<210> SEQ ID NO 20
<211> LENGTH: 125
<212> TYPE: PRT
<213> ORGANISM: Homo sapiens
```

<400> SEQUENCE: 20

Asp Ile Gln Met Thr Gln Ser Pro Ser Thr Leu Ala Ala Ser Ile Gly
1               5                   10                  15

Gly Thr Val Arg Val Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe Ile Phe Pro Pro Ser Asp Glu Gln
        115                 120                 125

<210> SEQ ID NO 21
<211> LENGTH: 132
<212> TYPE: PRT
<213> ORGANISM: Homo sapiens

<400> SEQUENCE: 21

Gln Val Gln Leu Gln Glu Ser Gly Pro Gly Leu Val Lys Pro Leu Glu
1               5                   10                  15

Thr Leu Ser Leu Thr Cys Asn Val Ser Gly Ala Phe Ile Ala Asp His
            20                  25                  30

Tyr Trp Ser Trp Ile Arg Leu Pro Leu Gly Lys Gly Pro Glu Trp Ile
        35                  40                  45

Gly Tyr Val His Asp Ser Gly Asp Ile Asn Tyr Asn Pro Ser Leu Lys
    50                  55                  60

Asn Arg Val His Leu Ser Leu Asp Lys Ser Thr Asn Gln Val Ser Leu
65                  70                  75                  80

Lys Leu Met Ala Val Thr Ala Gly Asp Ser Ala Leu Tyr Tyr Cys Ala
                85                  90                  95

Thr Thr Lys His Gly Arg Arg Ile Tyr Gly Val Val Ala Phe Gly Glu
            100                 105                 110

Trp Phe Thr Tyr Phe Tyr Met Asp Val Trp Gly Arg Gly Thr Thr Val
        115                 120                 125

Thr Val Ser Ser
    130

<210> SEQ ID NO 22
<211> LENGTH: 132
<212> TYPE: PRT
<213> ORGANISM: Homo sapiens

<400> SEQUENCE: 22

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Met Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys

```
                50                  55                  60
Ser Arg Val His Leu Ser Leu Asp Lys Ser Asn Asn Leu Val Ser Leu
 65                  70                  75                  80

Arg Leu Thr Ala Val Thr Ala Ala Asp Ser Ala Thr Tyr Tyr Cys Ala
                 85                  90                  95

Thr Thr Lys His Gly Arg Arg Ile Tyr Gly Ile Val Ala Phe Asn Glu
                100                 105                 110

Trp Phe Thr Tyr Phe Tyr Met Asp Val Trp Gly Lys Gly Thr Thr Val
                115                 120                 125

Thr Val Ser Ser
        130

<210> SEQ ID NO 23
<211> LENGTH: 132
<212> TYPE: PRT
<213> ORGANISM: Homo sapiens

<400> SEQUENCE: 23

Gln Val Gln Leu Gln Glu Ser Gly Pro Gly Leu Val Lys Pro Ser Glu
 1               5                  10                  15

Thr Leu Ser Leu Thr Cys Ser Val Ser Gly Ala Ser Ile Ser Asp Ser
                 20                  25                  30

Tyr Trp Ser Trp Ile Arg Arg Ser Pro Gly Lys Gly Leu Glu Trp Ile
                 35                  40                  45

Gly Tyr Val His Lys Ser Gly Asp Thr Asn Tyr Ser Pro Ser Leu Lys
     50                  55                  60

Ser Arg Val Asn Leu Ser Leu Asp Thr Ser Lys Asn Gln Val Ser Leu
 65                  70                  75                  80

Ser Leu Val Ala Ala Thr Ala Ala Asp Ser Gly Lys Tyr Tyr Cys Ala
                 85                  90                  95

Arg Thr Leu His Gly Arg Arg Ile Tyr Gly Ile Val Ala Phe Asn Glu
                100                 105                 110

Trp Phe Thr Tyr Phe Tyr Met Asp Val Trp Gly Asn Gly Thr Gln Val
                115                 120                 125

Thr Val Ser Ser
        130

<210> SEQ ID NO 24
<211> LENGTH: 132
<212> TYPE: PRT
<213> ORGANISM: Homo sapiens

<400> SEQUENCE: 24

Gln Val Gln Leu Gln Glu Ser Gly Pro Gly Leu Val Lys Pro Pro Glu
 1               5                  10                  15

Thr Leu Ser Leu Thr Cys Ser Val Ser Gly Ala Ser Val Asn Asp Ala
                 20                  25                  30

Tyr Trp Ser Trp Ile Arg Gln Ser Pro Gly Lys Arg Pro Glu Trp Val
                 35                  40                  45

Gly Tyr Val His His Ser Gly Asp Thr Asn Tyr Asn Pro Ser Leu Lys
     50                  55                  60

Arg Arg Val Thr Phe Ser Leu Asp Thr Ala Lys Asn Glu Val Ser Leu
 65                  70                  75                  80

Lys Leu Val Ala Leu Thr Ala Ala Asp Ser Ala Val Tyr Phe Cys Ala
                 85                  90                  95

Arg Ala Leu His Gly Lys Arg Ile Tyr Gly Ile Val Ala Leu Gly Glu
```

```
                    100                 105                 110
Leu Phe Thr Tyr Phe Tyr Met Asp Val Trp Gly Lys Gly Thr Thr Val
                115                 120                 125

Thr Val Ser Ser
        130

<210> SEQ ID NO 25
<211> LENGTH: 132
<212> TYPE: PRT
<213> ORGANISM: Homo sapiens

<400> SEQUENCE: 25

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
                20                  25                  30

Tyr Trp Ser Trp Ile Arg Gln Ser Pro Gly Lys Arg Pro Glu Trp Val
            35                  40                  45

Gly Tyr Val His His Ser Gly Asp Thr Asn Tyr Asn Pro Ser Leu Lys
        50                  55                  60

Arg Arg Val Thr Phe Ser Leu Asp Thr Ala Lys Asn Glu Val Ser Leu
65                  70                  75                  80

Lys Leu Val Asp Leu Thr Ala Ala Asp Ser Ala Val Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
                115                 120                 125

Thr Val Ser Ser
        130

<210> SEQ ID NO 26
<211> LENGTH: 132
<212> TYPE: PRT
<213> ORGANISM: Homo sapiens

<400> SEQUENCE: 26

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
                20                  25                  30

Tyr Trp Ser Trp Ile Arg Gln Ser Pro Gly Lys Arg Pro Glu Trp Val
            35                  40                  45

Gly Tyr Val His His Ser Gly Asp Thr Asn Tyr Asn Pro Ser Leu Lys
        50                  55                  60

Arg Arg Val Ser Phe Ser Leu Asp Thr Ala Lys Asn Glu Val Ser Leu
65                  70                  75                  80

Lys Leu Val Asp Leu Thr Ala Ala Asp Ser Ala Ile Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
                115                 120                 125

Thr Val Ser Ser
        130
```

```
<210> SEQ ID NO 27
<211> LENGTH: 132
<212> TYPE: PRT
<213> ORGANISM: Homo sapiens

<400> SEQUENCE: 27

Gln Val Gln Leu Val Glu Ser Gly Pro Gly Leu Val Thr Pro Ser Glu
1               5                   10                  15

Thr Leu Ser Leu Thr Cys Thr Val Ser Asn Gly Ser Val Ser Gly Arg
            20                  25                  30

Phe Trp Ser Trp Ile Arg Gln Ser Pro Gly Arg Gly Leu Glu Trp Ile
        35                  40                  45

Gly Tyr Phe Ser Asp Thr Asp Arg Ser Glu Tyr Ser Pro Ser Leu Arg
    50                  55                  60

Ser Arg Leu Thr Leu Ser Leu Asp Ala Ser Arg Asn Gln Leu Ser Leu
65                  70                  75                  80

Lys Leu Lys Ser Val Thr Ala Ala Asp Ser Ala Thr Tyr Tyr Cys Ala
                85                  90                  95

Arg Ala Gln Gln Gly Lys Arg Ile Tyr Gly Ile Val Ser Phe Gly Glu
            100                 105                 110

Phe Phe Tyr Tyr Tyr Met Asp Ala Trp Gly Lys Gly Thr Ala Val
        115                 120                 125

Thr Val Ser Ser
    130

<210> SEQ ID NO 28
<211> LENGTH: 132
<212> TYPE: PRT
<213> ORGANISM: Homo sapiens

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ser Val Ser Asn Gly Ser Val Ser Gly Arg
            20                  25                  30

Phe Trp Ser Trp Ile Arg Gln Ser Pro Gly Arg Gly Leu Glu Trp Ile
        35                  40                  45

Gly Tyr Phe Ser Asp Thr Glu Lys Ser Asn Tyr Asn Pro Ser Leu Arg
    50                  55                  60

Ser Arg Leu Thr Leu Ser Val Asp Ala Ser Lys Asn Gln Leu Ser Leu
65                  70                  75                  80

Lys Leu Asn Ser Val Thr Ala Ala Asp Ser Ala Thr Tyr Tyr Cys Ala
                85                  90                  95

Arg Thr Gln Gln Gly Lys Arg Ile Tyr Gly Val Val Ser Phe Gly Glu
            100                 105                 110

Phe Phe His Tyr Tyr Met Asp Ala Trp Gly Lys Gly Thr Ala Val
        115                 120                 125

Thr Val Ser Ser
    130

<210> SEQ ID NO 29
<211> LENGTH: 132
<212> TYPE: PRT
<213> ORGANISM: Homo sapiens

<400> SEQUENCE: 29

Gln Val Gln Leu Gln Glu Ser Gly Pro Gly Leu Val Lys Pro Ser Glu
1               5                   10                  15
```

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
            35                  40                  45

Gly Tyr Ile Ser Asp Arg Glu Ser Ala Thr Tyr Asn Pro Ser Leu Asn
50                  55                  60

Ser Arg Val Val Ile Ser Arg Asp Thr Ser Thr Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Arg Gly Thr Thr Val
            115                 120                 125

Thr Val Ser Ser
    130

<210> SEQ ID NO 30
<211> LENGTH: 132
<212> TYPE: PRT
<213> ORGANISM: Homo sapiens

<400> SEQUENCE: 30

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
            35                  40                  45

Gly Tyr Ile Ser Asp Arg Ala Ser Ala Thr Tyr Asn Pro Ser Leu Asn
50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
            115                 120                 125

Thr Val Ser Ser
    130

<210> SEQ ID NO 31
<211> LENGTH: 132
<212> TYPE: PRT
<213> ORGANISM: Homo sapiens

<400> SEQUENCE: 31

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
            35                  40                  45

Gly Tyr Ile Ser Asp Arg Glu Ser Ala Thr Tyr Asn Pro Ser Leu Asn
50                  55                  60

```
Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
            115                 120                 125

Thr Val Ser Ser
    130

<210> SEQ ID NO 32
<211> LENGTH: 132
<212> TYPE: PRT
<213> ORGANISM: Homo sapiens

<400> SEQUENCE: 32

Gln Val Gln Leu Gln Glu Ser Gly Pro Gly Leu Val Lys Pro Ser Glu
  1               5                  10                  15

Thr Leu Ser Val Thr Cys Ser Val Ser Gly Asp Ser Met Asn Asn Ser
                 20                  25                  30

Tyr Trp Thr Trp Ile Arg Gln Ser Pro Gly Lys Gly Leu Glu Trp Ile
             35                  40                  45

Gly Tyr Ile Ser Lys Ser Glu Ser Ala Asn Tyr Asn Pro Ser Leu Asn
 50                  55                  60

Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg His Gly Gln Arg Ile Tyr Gly Val Val Ser Phe Gly Glu
            100                 105                 110

Phe Phe Thr Tyr Tyr Ser Met Asp Val Trp Gly Lys Gly Thr Thr Val
            115                 120                 125

Thr Val Ser Ser
    130

<210> SEQ ID NO 33
<211> LENGTH: 105
<212> TYPE: PRT
<213> ORGANISM: Homo sapiens

<400> SEQUENCE: 33

Ser Ser Met Ser Val Ser Pro Gly Glu Thr Ala Lys Ile Thr Cys Gly
  1               5                  10                  15

Glu Lys Ser Ile Gly Ser Arg Ala Val Gln Trp Tyr Gln Lys Lys Pro
                 20                  25                  30

Gly Gln Pro Pro Ser Leu Ile Ile Tyr Asn Asn Gln Asp Arg Pro Ser
             35                  40                  45

Gly Val Pro Glu Arg Phe Ser Ala Ser Pro Asp Ile Glu Phe Gly Thr
 50                  55                  60

Thr Ala Thr Leu Thr Ile Thr Asn Val Glu Ala Gly Asp Glu Ala Asp
 65                  70                  75                  80

Tyr Tyr Cys His Ile Tyr Asp Ala Arg Arg Pro Thr Asn Trp Val Phe
                 85                  90                  95

Asp Arg Gly Thr Thr Leu Thr Val Leu
            100                 105
```

<210> SEQ ID NO 34
<211> LENGTH: 105
<212> TYPE: PRT
<213> ORGANISM: Homo sapiens

<400> SEQUENCE: 34

Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Ser
            20                  25                  30

Gly Gln Pro Pro Ser Leu Ile Ile Tyr Asn Asn Gln Asp Arg Pro Ser
        35                  40                  45

Gly Val Pro Glu Arg Phe Ser Ala Thr Pro Asp Phe Gly Ala Gly Thr
    50                  55                  60

Thr Ala Thr Leu Thr Ile Thr Asn Val Glu Ala Asp Asp Glu Ala Asp
65                  70                  75                  80

Tyr Tyr Cys His Ile Tyr Asp Ala Arg Gly Gly Thr Asn Trp Val Phe
                85                  90                  95

Asp Arg Gly Ala Thr Leu Thr Val Leu
            100                 105

<210> SEQ ID NO 35
<211> LENGTH: 105
<212> TYPE: PRT
<213> ORGANISM: Homo sapiens

<400> SEQUENCE: 35

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 36
<211> LENGTH: 105
<212> TYPE: PRT
<213> ORGANISM: Homo sapiens

<400> SEQUENCE: 36

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Met Tyr Asn Asn His Asp Arg Pro Ser
        35                  40                  45

Gly Ile Pro Glu Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 37
<211> LENGTH: 105
<212> TYPE: PRT
<213> ORGANISM: Homo sapiens

<400> SEQUENCE: 37

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
                20                  25                  30

Gly Gln Ala Pro Ser Leu Ile Ile Tyr Asn Asn Asn Asp Arg Pro Ser
            35                  40                  45

Gly Ile Pro Glu Arg Phe Ser Gly Ser Pro Gly Ser Thr Phe Gly Thr
        50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 38
<211> LENGTH: 105
<212> TYPE: PRT
<213> ORGANISM: Homo sapiens

<400> SEQUENCE: 38

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
                20                  25                  30

Gly Gln Ala Pro Ser Leu Ile Ile Tyr Asn Asn Asn Asp Arg Pro Ser
            35                  40                  45

Gly Ile Pro Glu Arg Phe Ser Gly Ser Pro Gly Ser Thr Phe Gly Thr
        50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 39
<211> LENGTH: 108
<212> TYPE: PRT
<213> ORGANISM: Homo sapiens

<400> SEQUENCE: 39

Ser Tyr Val Arg Pro Leu Ser Val Ala Leu Gly Glu Thr Ala Ser Ile
1               5                   10                  15

Ser Cys Gly Arg Gln Ala Leu Gly Ser Arg Ala Val Gln Trp Tyr Gln

```
            20                  25                  30
His Arg Pro Gly Gln Ala Pro Ile Leu Leu Ile Tyr Asn Asn Gln Asp
         35                  40                  45

Arg Pro Ser Gly Ile Pro Glu Arg Phe Ser Gly Thr Pro Asp Ile Asn
 50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                 85                  90                  95

Trp Ser Phe Gly Gly Ala Thr Arg Leu Thr Val Leu
            100                 105

<210> SEQ ID NO 40
<211> LENGTH: 108
<212> TYPE: PRT
<213> ORGANISM: Homo sapiens

<400> SEQUENCE: 40

Ser Tyr Val Arg Pro Leu Ser Val Ala Leu Gly Glu Thr Ala Arg Ile
 1               5                  10                  15

Ser Cys Gly Arg Gln Ala Leu Gly Ser Arg Ala Val Gln Trp Tyr Gln
             20                  25                  30

His Arg Pro Gly Gln Ala Pro Ile Leu Leu Ile Tyr Asn Asn Gln Asp
         35                  40                  45

Arg Pro Ser Gly Ile Pro Glu Arg Phe Ser Gly Thr Pro Asp Ile Asn
 50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                 85                  90                  95

Trp Ser Phe Gly Gly Ala Thr Arg Leu Thr Val Leu
            100                 105

<210> SEQ ID NO 41
<211> LENGTH: 108
<212> TYPE: PRT
<213> ORGANISM: Homo sapiens

<400> SEQUENCE: 41

Ser Tyr Val Arg Pro Leu Ser Val Ala Leu Gly Glu Thr Ala Arg Ile
 1               5                  10                  15

Ser Cys Gly Arg Gln Ala Leu Gly Ser Arg Ala Val Gln Trp Tyr Gln
             20                  25                  30

His Arg Pro Gly Gln Ala Pro Ile Leu Leu Ile Tyr Asn Asn Gln Asp
         35                  40                  45

Arg Pro Ser Gly Ile Pro Glu Arg Phe Ser Gly Thr Pro Asp Ile Asn
 50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                 85                  90                  95

Trp Ser Phe Gly Gly Ala Thr Arg Leu Thr Val Leu
            100                 105

<210> SEQ ID NO 42
<211> LENGTH: 107
<212> TYPE: PRT
```

<213> ORGANISM: Homo sapiens

<400> SEQUENCE: 42

Ser Ser Leu Pro Leu Ser Val Ala Pro Gly Ala Thr Ala Lys Ile Ala
1               5                   10                  15
Cys Gly Glu Lys Ser Phe Ala Ser Arg Ala Val Gln Trp Tyr Gln Gln
            20                  25                  30
Lys Pro Gly Gln Ala Pro Val Leu Ile Ile Tyr Asn Asn Gln Asp Arg
        35                  40                  45
Pro Ala Gly Val Ser Glu Arg Phe Ser Gly Thr Pro Asp Val Gly Phe
    50                  55                  60
Gly Ser Thr Ala Thr Leu Thr Ile Ser Arg Val Glu Ala Gly Asp Glu
65                  70                  75                  80
Ala Asp Tyr Tyr Cys His Lys Trp Asp Ser Arg Ser Pro Leu Ser Trp
                85                  90                  95
Val Phe Gly Gly Gly Thr Gln Leu Thr Val Leu
            100                 105

<210> SEQ ID NO 43
<211> LENGTH: 107
<212> TYPE: PRT
<213> ORGANISM: Homo sapiens

<400> SEQUENCE: 43

Ser Ser Leu Pro Leu Ser Leu Ala Pro Gly Ala Thr Ala Lys Ile Pro
1               5                   10                  15
Cys Gly Glu Lys Ser Arg Gly Ser Arg Ala Val Gln Trp Tyr Gln Gln
            20                  25                  30
Lys Pro Gly Gln Ala Pro Thr Leu Ile Ile Tyr Asn Asn Gln Asp Arg
        35                  40                  45
Pro Ala Gly Val Ser Glu Arg Tyr Ser Gly Asn Pro Asp Val Ala Ile
    50                  55                  60
Gly Val Thr Ala Thr Leu Thr Ile Ser Arg Val Glu Ala Gly Asp Glu
65                  70                  75                  80
Ala Glu Tyr Tyr Cys His Tyr Trp Asp Ser Arg Ser Pro Ile Ser Trp
                85                  90                  95
Val Phe Gly Gly Trp Thr Gln Leu Thr Val Leu
            100                 105

<210> SEQ ID NO 44
<211> LENGTH: 18
<212> TYPE: DNA
<213> ORGANISM: Artificial Sequence
<220> FEATURE:
<223> OTHER INFORMATION: syntheszed

<400> SEQUENCE: 44
cccaccaaca rgcrgcct                                                 18

<210> SEQ ID NO 45
<211> LENGTH: 20
<212> TYPE: DNA
<213> ORGANISM: Homo sapiens

<400> SEQUENCE: 45
taatggcagc aatttcacca                                               20

<210> SEQ ID NO 46
<211> LENGTH: 21

```
<212> TYPE: DNA
<213> ORGANISM: Artificial Sequence
<220> FEATURE:
<223> OTHER INFORMATION: synthesized

<400> SEQUENCE: 46
gaatgccaaa ttcctgcttg a                                              21

<210> SEQ ID NO 47
<211> LENGTH: 29
<212> TYPE: DNA
<213> ORGANISM: Artificial Sequence
<220> FEATURE:
<223> OTHER INFORMATION: synthesized

<400> SEQUENCE: 47
ggcttaggca tctcctatgg caggaagaa                                      29

<210> SEQ ID NO 48
<211> LENGTH: 37
<212> TYPE: DNA
<213> ORGANISM: Artificial Sequence
<220> FEATURE:
<223> OTHER INFORMATION: synthesized

<400> SEQUENCE: 48
ggtgtgtagt tctgccaatc agggaagwag ccttgtg                             37

<210> SEQ ID NO 49
<211> LENGTH: 28
<212> TYPE: DNA
<213> ORGANISM: Artificial Sequence
<220> FEATURE:
<223> OTHER INFORMATION: synthesized

<400> SEQUENCE: 49
tagaaagagc agaagacagt ggcaatga                                       28

<210> SEQ ID NO 50
<211> LENGTH: 48
<212> TYPE: DNA
<213> ORGANISM: Artificial Sequence
<220> FEATURE:
<223> OTHER INFORMATION: synthesized

<400> SEQUENCE: 50
tcatcaatgg tggtgatgat gatgttttc tctctgcacc actcttct                  48

<210> SEQ ID NO 51
<211> LENGTH: 21
<212> TYPE: DNA
<213> ORGANISM: Artificial Sequence
<220> FEATURE:
<223> OTHER INFORMATION: synthesized

<400> SEQUENCE: 51
gttggaccaa gctatgcagg t                                              21

<210> SEQ ID NO 52
<211> LENGTH: 20
<212> TYPE: DNA
<213> ORGANISM: Artificial Sequence
<220> FEATURE:
<223> OTHER INFORMATION: synthesized

<400> SEQUENCE: 52
```
agaagcgttt ggcaatgtgc                                                      20

<210> SEQ ID NO 53
<211> LENGTH: 30
<212> TYPE: DNA
<213> ORGANISM: Artificial Sequence
<220> FEATURE:
<223> OTHER INFORMATION: synthesized

<400> SEQUENCE: 53
ttgggatgac gcactgctgc atcaacccca                                           30

<210> SEQ ID NO 54
<211> LENGTH: 487
<212> TYPE: PRT
<213> ORGANISM: Homo sapiens

<400> SEQUENCE: 54

Thr Met Gly Trp Ser Cys Ile Ile Leu Phe Leu Val Ala Thr Ala Thr
1               5                   10                  15

Gly Val His Ser Gln Glu Gln Leu Val Glu Ser Gly Gly Gly Val Val
                20                  25                  30

Gln Pro Gly Gly Ser Leu Arg Leu Ser Cys Leu Ala Ser Gly Phe Thr
            35                  40                  45

Phe His Lys Tyr Gly Met His Trp Val Arg Gln Ala Pro Gly Lys Gly
        50                  55                  60

Leu Glu Trp Val Ala Leu Ile Ser Asp Asp Gly Met Arg Lys Tyr His
65                  70                  75                  80

Ser Asp Ser Met Trp Gly Arg Val Thr Ile Ser Arg Asp Asn Ser Lys
                85                  90                  95

Asn Thr Leu Tyr Leu Gln Phe Ser Ser Leu Lys Val Glu Asp Thr Ala
            100                 105                 110

Met Phe Phe Cys Ala Arg Glu Ala Gly Gly Pro Ile Trp His Asp Asp
        115                 120                 125

Val Lys Tyr Tyr Asp Phe Asn Asp Gly Tyr Tyr Asn Tyr His Tyr Met
130                 135                 140

Asp Val Trp Gly Lys Gly Thr Thr Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

-continued

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
        340                 345                 350

Trp Leu Asn Gly Lys Glu Tyr Lys Cys Lys Val Ser Asn Lys Ala Leu
    355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
            405                 410                 415

Ile Ala Val Glu Trp Glu Ser Asn Gly Gln Pro Glu Asn Asn Tyr Lys
        420                 425                 430

Thr Thr Pro Pro Val Leu Asp Ser Asp Gly Ser Phe Phe Leu Tyr Ser
    435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly Lys
            485

<210> SEQ ID NO 55
<211> LENGTH: 236
<212> TYPE: PRT
<213> ORGANISM: Homo sapiens

<400> SEQUENCE: 55

Thr Met Gly Trp Ser Cys Ile Ile Leu Phe Leu Val Ala Thr Ala Thr
1               5                   10                  15

Gly Ser Val Thr Gln Ser Ala Leu Thr Gln Pro Ala Ser Val Ser Gly
            20                  25                  30

Ser Pro Gly Gln Thr Ile Thr Ile Ser Cys Asn Gly Thr Ser Ser Asp
        35                  40                  45

Val Gly Gly Phe Asp Ser Val Ser Trp Tyr Gln Gln Ser Pro Gly Lys
    50                  55                  60

Ala Pro Lys Val Met Val Phe Asp Val Ser His Arg Pro Ser Gly Ile
65                  70                  75                  80

Ser Asn Arg Phe Ser Gly Ser Lys Ser Gly Asn Thr Ala Ser Leu Thr
            85                  90                  95

Ile Ser Gly Leu His Ile Glu Asp Glu Gly Asp Tyr Phe Cys Ser Ser
        100                 105                 110

Leu Thr Asp Arg Ser His Arg Ile Phe Gly Gly Gly Thr Lys Val Thr
    115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
            165                 170                 175

Ser Pro Val Lys Ala Gly Val Glu Thr Thr Thr Pro Ser Lys Gln Ser
        180                 185                 190

```
Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

COMBINATION OF BROADLY NEUTRALIZING HIV ANTIBODIES AND VIRAL INDUCERS

CROSS REFERENCE TO RELATED APPLICATION

This application is a divisional of U.S. patent application Ser. No. 15/327,725, filed Jan. 20, 2017, which issued as U.S. Pat. No. 10,676,521 on Jun. 9, 2020, which is the U.S. National Phase of International Application No. PCT/US2015/041272, filed Jul. 21, 2015, which claims priority to U.S. Provisional Application No. 62/026,915 filed on Jul. 21, 2014. The content of the applications are incorporated herein by reference in their entirety.

GOVERNMENT INTERESTS

The invention disclosed herein was made, at least in part, with Government support under Grant Nos. T32GM07739, AI100663-02, AI100148-02, AI081677-05, and #8 UL1 TR000043 from the National Institutes of Health (NIH). Accordingly, the U.S. Government has certain rights in this invention.

FIELD OF THE INVENTION

This invention relates to methods and agents for prevention or disruption of the establishment or maintenance of human immunodeficiency virus latent reservoirs.

BACKGROUND OF THE INVENTION

Human immunodeficiency virus (HIV) is a retrovirus that causes acquired immunodeficiency syndrome (AIDS). HIV-1 is the most common and pathogenic strain of the virus. Although HIV-1 infection can be suppressed with any one of several different combination anti-retroviral therapies (ART), such a therapy must be maintained for the life of a patient because it does not eliminate a reservoir of latently infected cells even after years of ART (Siliciano, et al., Nat Med, 2003. 9(6): pp. 727-8.). As a result, ART termination follows by rapid viral rebound (Davey, et al., Proc. Natl. Acad. Sci. U.S.A. 1999. pp. 15109-15114). To date, all attempts to alter the reservoir by intensifying ART, by including additional anti-retroviral drugs (Dinoso, et al., Proc Natl Acad Sci USA, 2009. 106(23) pp. 9403-8 and Gandhi, et al., PLoS Med, 2010. 7(8)), or by administration of global T-cell activators or inducers of viral transcription, in the presence of ART, have failed (Archin, et al., J. Infect. Dis. 2014. pp. 1-26; Dybul, et al., Infect Dis, 2002. 185(1): pp. 61-8; Lafeuillade, et al., J Acquir Immune Defic Syndr, 2001. 26(1): p. 44-55; and Prins, et al., AIDS, 1999. 13(17): p. 2405-10). Thus, there is a need for methods and agents for prevention or disruption of the establishment or maintenance of HIV-1 latent reservoirs.

SUMMARY OF INVENTION

This invention relates to using broadly neutralizing antibodies (bNAbs) alone or in combination with viral transcription inducers in preventing the establishment of the latent reservoirs of HIV-1 infected cells or decreasing the size of the reservoir, and thereby addresses the need mentioned above.

Accordingly, one aspect of this invention provides a method for decreasing the size of or preventing the establishment of a latent reservoir of HIV infected cells (e.g., a cell population comprising HIV-infected $CD4^+$ T cells.) in a subject in need thereof. The method includes administering to the subject a therapeutically effective amount of an isolated anti-HIV antibody, e.g., a bNAb, and administering to the subject two or more viral transcription inducers in effective amounts to induce transcription of an HIV provirus in the cells.

The antibody can be a human antibody, a humanized antibody, or a chimeric antibody. In one example, the antibody is antibody 3BNC117, 10-1074, or PG16, or any other described below, or combination thereof. Preferably, two or three of the antibodies 3BNC117, 10-1074, and PG16 are administered to the subject. The antibody or antibodies can be administered to the subject within about 96 hours or earlier (e.g., 72, 48, 36, 24, or 12 hours) after exposure or suspected exposure to HIV. The transcription inducers can be administered to the subject for a period of about 5-14 days (e.g., 6-13, 7-12, 8, 9, 10, 11, 12 days). Examples of the transcription inducers include vorinostat, an HDAC inhibitor, I-BET151, a BET bromodomain inhibitor, and αCTLA4, a T-cell inhibitory pathway blocker. The method can further comprise administering to the subject an antiviral agent, such as one selected from the group consisting of a non-nucleoside reverse transcriptase inhibitor, a protease inhibitor, an entry or fusion inhibitor, and an integrase inhibitor.

In a second aspect, the invention provides a kit comprising an isolated anti-HIV antibody, a first viral transcription inducer, and a second viral transcription inducer. The kit can contain one, two, three, or more of antibodies 3BNC117, 10-1074, PG16, and those described below. The antibody can be a human antibody, a humanized antibody, or a chimeric antibody. The transcription inducers can be selected from the group consisting of vorinostat, an HDAC inhibitor, I-BET151, a BET bromodomain inhibitor, and αCTLA4, a T-cell inhibitory pathway blocker. In the kit, the first viral transcription inducer and the second viral transcription inducer can be contained in one pharmaceutical composition or in two separate pharmaceutical compositions. The kit can further contain an antiviral agent, which can be selected from the group consisting of a non-nucleoside reverse transcriptase inhibitor, a protease inhibitor, an entry or fusion inhibitor, and an integrase inhibitor. The kit can be used in the method of this invention.

In a third aspect, the invention features a method for preventing the establishment of a latent reservoir of HIV infected cells in a subject in need thereof. The method includes administering to the subject a therapeutically effective amount of an isolated anti-HIV antibody. The antibody can be a human antibody, a humanized antibody, or a chimeric antibody. In one example, the antibody is antibody 3BNC117, 10-1074, PG16, any of those described below, or a combination thereof. Preferably, two, three, or more of the antibodies are administered to the subject. The antibody or antibodies can be administered to the subject within about 96 hours or earlier (e.g., 72, 48, 36, 24, or 12 hours) after exposure or suspected exposure to HIV.

The details of one or more embodiments of the invention are set forth in the description below. Other features, objectives, and advantages of the invention will be apparent from the description and from the claims.

BRIEF DESCRIPTION OF THE DRAWINGS

(FIG. 1A) Schematic timeline for the bNAb (top) and ART (bottom) experiments. (FIG. 1B) Plasma viremia for untreated mice. The x-axis is in days post HIV-1 challenge. The y-axis is viral RNA copies/ml. Gray shading indicates values beneath the detection limit of 800 copies/ml. The blue line indicates the geometric mean plasma viremia. (FIG. 1C) Plasma viremia for ART-treated mice as in FIG. 1B. The blue shading indicates the treatment period with ART. (FIG. 1D) Plasma viremia for antibody-treated mice. The red arrows indicate antibody tri-mix injections. The dashed red line shows average plasma antibody concentration for all mice in the group. (FIG. 1E) Graph as in FIG. 1D, for mice treated with antibody starting 8 days after HIV-1 challenge. (FIG. 1F) Percentage of CD4$^+$ T cells in the spleen at the terminal point measured by flow cytometry, organized by treatment group. (A=aviremic, V=viremic). (FIG. 1G) Cell-associated HIV-1 RNA measured in spleen T cells at the terminal point, plotted as the ratio of HIV-1 RNA to CCR5 copies for each mouse. Gray shading indicates the detection limit of $1.25 \times 10^{-5}$ copies per cell. (FIG. 1H) Cell-associated HIV-1 DNA measured in spleen T cells at the terminal point, plotted as the ratio of HIV-1 RNA to CCR5 copies for each mouse. Gray shading indicates the detection limit of $2.0 \times 10^{-5}$ copies per cell.

FIG. 2A, FIG. 2B, FIG. 2C, and FIG. 2D are a set of diagrams showing that FcR$^{null}$ antibodies suppress viremia but do not prevent rebound: (FIG. 2A) Plasma viremia as in FIG. 1D for mice treated with FcR$^{null}$ tri-mix. (FIG. 2B) The proportion of mice that were viremic at the terminal point for each treatment group (*, p<0.05; Fisher's Exact test). (FIG. 2C) For all viremic mice, plasma antibody concentration on the day of viral rebound. Antibody levels were significantly higher in FcR$^{null}$ tri-mix treated mice compared to wild-type tri-mix treated mice (*, p<0.05; **, p<0.01; Mann-Whitney test). (FIG. 2D) Sequences of gp120 cloned from plasma. Horizontal lines denote individual clones, grouped by mouse, shown on the right. Red ticks and green ticks indicate non-synonymous and synonymous substitutions relative to gp120$_{YU2}$, respectively. Blue shading highlights sites of mutations that confer escape to the antibody tri-mix.

(FIG. 3A) Schematic timeline of the experiment. (FIG. 3B, FIG. 3C, and FIG. 3D) Graphs show plasma viremia for individual mice on the left y-axis, geometric mean antibody level on the right y-axis among all mice in the group (red). The x-axis represents days relative to the first antibody injection. Antibody injections are indicated with red arrows. Mice that had rebound plasma viremia are shown in gray. Mice that failed to rebound are shown in black. (FIG. 3B) Mice that received tri-mix antibodies, but no inducers. (FIG. 3C) Mice that received tri-mix antibodies and vorinostat (green arrows). (FIG. 3D) Mice that received tri-mix antibodies and I-BET151 (purple shading). (FIG. 3E) Mice that received tri-mix antibodies and αCTLA4 (orange arrows).

(FIG. 4A) Mice treated with tri-mix of antibodies, and a combination of three inducers. Graph, arrows, and shading are as in FIG. 3. (FIG. 4B) Graph shows the proportion of mice that showed rebound viremia for each treatment group, where all mice that received antibody tri-mix and any one of the three single inducers (shown in FIGS. 3C, 3D, and 3E) are pooled together (*, p<0.05; Mann-Whitney test).

FIG. 5A, FIG. 5B, FIG. 5C, FIG. 5D, FIG. 5E, FIG. 5F, and FIG. 5G are a set of diagrams showing antibody persistence and premature termination do not account for non-rebounding: (FIG. 5A) Percentage of CD4$^+$ T cells at the terminal point measured in the spleen by flow cytometry. (FIG. 5B) Cell-associated HIV-1 RNA measured in spleen cells at terminal point, plotted as the ratio of HIV-1 RNA to CCR5 DNA copies for each mouse. Mice that had measureable HIV-1 RNA, but undetectable CCR5 DNA are plotted as $10^4$ copies per cell. (FIG. 5C) Plasma viremia before therapy was initiated for each mouse, organized by treatment group and rebound status (N.R.=non-rebounder, Reb.=viral rebounder). There was no significant difference for any individual group (Kruskal-Wallis test). (FIG. 5D) The plasma antibody level at the time of viral rebound for each mouse that rebounded, organized by treatment group. The mean plasma antibody level at the time of rebound was 2.97 µg/ml for all groups. (FIG. 5E) For each mouse that rebounded, the number of days that elapsed from when the antibody level dropped below 2.97 µg/ml to the time of rebound. (FIG. 5F) For mice that did not rebound, the number of days that elapsed from when each mouse's antibody levels dropped below 2.97 µg/ml to the terminal point. (FIG. 5G) Cell-associated HIV-1 DNA measured in spleen T cells at the terminal point, plotted as the ratio of HIV-1 DNA to CCR5 copies for each mouse. Mice that had measureable HIV-1 DNA, but undetectable CCR5 DNA are plotted as $10^4$ copies per cell.

(FIG. 6A) Each mouse shown in FIG. 1D is shown individually. (FIG. 6B) Each mouse shown in FIG. 1E is shown individually.

FIG. 8A, FIG. 8B, FIG. 8C, and FIG. 8D are a set of diagram showing viremia and antibody levels in individual mice (antibody only and antibody plus single inducers) in FIGS. 3A-3D: (FIG. 8A) Each mouse shown in FIG. 3A is shown individually. (FIG. 8B) Each mouse shown in FIG. 3B is shown individually. (FIG. 8C) Each mouse shown in FIG. 3C is shown individually. (FIG. 8D) Each mouse shown in FIG. 3D is shown individually.

(FIG. 10A) Graphs shown as in FIG. 4A. The blue line indicates the geometric mean viremia across all mice. (FIG. 10B) Proportion of human CD45$^+$ leukocytes in peripheral blood, measured by flow cytometry. (FIG. 10C) Percentage of CD4$^+$ T cells in the peripheral blood measured by flow cytometry.

DETAILED DESCRIPTION OF THE INVENTION

Figure 1A:
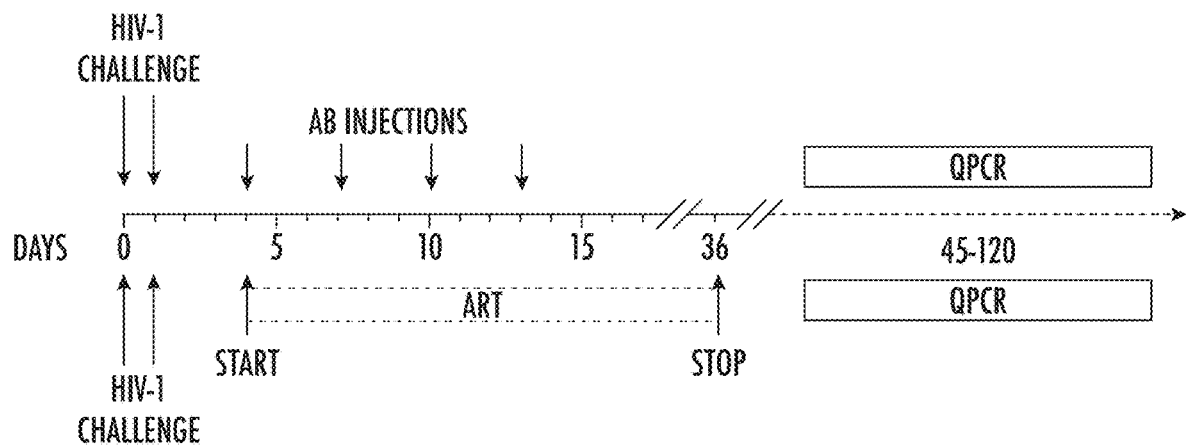
FIG. 1A, FIG. 1B, FIG. 1C, FIG. 1D, FIG. 1E, FIG. 1F, FIG. 1G, and FIG. 1H are a set of diagrams showing post-exposure prophylaxis with bNAbs.

This invention is based, at least in part, on unexpected discoveries (i) that bNAbs are more effective than ART in preventing the establishment of the latent reservoirs of HIV-1 infected cells by a mechanism that requires Fc receptor function and (ii) that bNAbs in combination with viral transcription inducers that act by independent mechanisms synergize to decrease the size of the reservoir as measured by prevention of viral rebound. Thus, combinations of viral transcription inducers and bNAbs constitute a therapeutic strategy that impacts the establishment and maintenance of the HIV-1 reservoir.

A. HIV-1 Latent Reservoir

HIV-1 viruses are transmitted as single-stranded, positive-sense, enveloped RNA viruses. Upon entry into a target host cell, the viral RNA genome is reverse transcribed into double-stranded DNA by a virally encoded reverse transcriptase that is transported along with the viral genome in the virus particle. The resulting viral DNA is then imported into the cell nucleus and integrated into the cellular DNA by a virally encoded integrase and host co-factors. Once integrated, the virus may become latent, allowing the virus and its host cell to avoid detection by the immune system. HIV-1 persists in infected individuals in a stable pool or reservoir of resting CD4$^+$ T cells and other cells as a latent but replication-competent provirus. Accordingly, as used herein, the term "latent reservoir" refers to cells or sites in a host that are latently infected with a microbe (e.g., HIV). Its presence and size of a HIV latent reservoir can be measured or assessed by viral rebound after terminating therapy as disclosed in the examples below.

Such a latent reservoir of HIV-1 infected cells cannot be cleared by combined ART and remains the major barrier to curing HIV-1 infection. In humans, macaques and humanized mice, the latent reservoir is established within days of initial infection and persists for the lifetime of the individual, making ART a lifelong necessity. While the latent reservoir's exact cellular composition is debated, it is generally believed that it consists primarily of CD4$^+$ memory T cells harboring replication competent provirus that is transcriptionally silenced. Because these cells have very long half-lives and may be able to undergo homeostatic proliferation, a "shock and kill" approach has been proposed to eradicate this reservoir by combining ART with inducers of viral transcription. However, all attempts at altering the HIV-1 reservoir have failed to date.

As disclosed herein, bNAbs can be used in preventing the establishment of the reservoir by a mechanism that requires Fc receptor function. In established infection bNAbs plus single inducers are ineffective in decreasing the reservoir size. Surprisingly, bNAbs plus a combination of inducers that act by independent mechanisms synergize to decrease the size of the reservoir as measured by prevention of viral rebound. Thus, combinations of inducers and bNAbs constitute a therapeutic strategy that can be used to prevent or disrupt the establishment and maintenance of the HIV-1 reservoir in humans and related animal models.

B. Antibodies

The invention disclosed herein involves broadly neutralizing HIV-1 antibodies. These antibodies refer to a class of neutralizing antibodies that neutralize multiple HIV-1 viral strains. Various bNAbs are known in the art and can be used in this invention. Examples include but are not limited to those described in U.S. Pat. No. 8,673,307, WO 2014063059, WO2012158948, and U.S. Provisional Application 61/934,359, including antibodies 3BNC117, 3BNC60, 12A12, 12A21, NIH45-46, bANC131, 8ANC134, IB2530, INC9, 8ANC195, 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 2012. 492(7427): p. 118 - - - 22, Horwitz et al., Proc Natl Acad Sci USA, 2013. 110(41): p. 16538 - - - 43, Scheid, et al. 2011. *Science,* 333:1633-1637, Scheid, et al. 2009. *Nature,* 458:636-640, Eroshkin et al., Nucleic Acids Res. 2014 January; 42 (Database issue):D1133-9, Mascola et al. Immunol Rev. 2013 July; 254(1):225-44, such as those listed below.

TABLE 1

| Viral Epitope | Antibody binding characteristics | Antibody clonal family |
|---|---|---|
| MPER of gp41 | Contiguous sequence | 2F5 |
|  | Contiguous sequence | 4E10 |
|  | Contiguous sequence | M66.6 |
|  | Contiguous sequence | CAP206-CH12 |
|  | Contiguous sequence | 10E8 1 |
| V1V2-glycan | Peptidoglycan | PG9, PG16 |
|  | Peptidoglycan | CH01-04 |
|  | Peptidoglycan | PGT 141-145 |
| Outer domain glycan | Glycan only | 2G12 |
| V3-glycan | Peptidoglycan | PGT121-123 |
|  | Peptidoglycan | PGT125-131 |
|  | Peptidoglycan | PGT135-137 |
| CD4 binding site | CDRH3 loop | b12 |
|  | No liganded structure | HJ16 |
|  | CDRH3 loop | CH103-106 |
|  | Mimics CD4 via CDRH2 | VRC01-03 |
|  | Mimics CD4 via CDRH2 | VRC-PG04, 04b |
|  | Mimics CD4 via CDRH2 | VRC-CH30-34 |
|  | No liganded structure | 3BNC117, 3BNC60 |
|  | Mimics CD4 via CDRH2 | NIH45-46 |
|  | No liganded structure | 12A12, 12A21 |
|  | No liganded structure | 8ANC131, 134 |
|  | No liganded structure | 1NC9, 1B2530 |

Listed below are the heavy chain variable regions (HC) sequences and light chain variable regions (LC) of some of the antibodies mentioned above, where the CDRs are in bold.

| Antibody | Sequence | SEQ ID NO: |
|---|---|---|
| 3BNC117HC | QVQLLQSGAAVTKPGASVRVSCEASGYNIRDYFIHWWRQAP GQGLQWVGWINPKTGQPNNPRQFQGRVSLTRHASWDFDTFS FYMDLKALRSDDTAVYFCARQRSDYWDFDVWGSGTQVTVSS ASTKG | 1 |
| 3BNC117kc | DIQMTQSPSSLSASVGDTVTITCQANGYLNWYQQRRGKAPK LLIYDGSKLERGVPSRFSGRRWGQEYNLTINNLQPEDIATY FCQVYEFVVPGTRLDLKRTVAAPSVFIFPPSD | 2 |
| 3BNC60HC | QVHLSQSGAAVTKPGASVRVSCEASGYKISDHFIHWWRQAP GQGLQWVCWINPKTGQPNNPRQFQGRVSLTRQASWDFDTYS FYMDLKAVRSDDTAIYFCARQRSDFWDFDVWGSGTQVTVSS ASTKG | 3 |

-continued

| Antibody | Sequence | SEQ ID NO: |
|---|---|---|
| 3BNC60KC | DIQMTQSPSSLSARVGDTVTITCQANGYLNWYQQRRGKAPK LLIYDGSKLERGVPARFSGRRWGQEYNLTINNLQPEDVATY FCQVYEFIVPGTRLDLKRTVAA | 4 |
| 12A12HC | SQQLVQSGTQVKKPGASVRISCQASGYSFTDYVLHWWRQAP GQGLEWMGWIKPVYGARNYARRFQGRINFDRDIYREIAFMD LSGLRSDDTALYFCARDSGDDTSWHLDPWGQGTLVIVSAA STKG | 5 |
| 12a12kc | DIQMTQSPSSLSASVGDRVTITCQAGQGIGSSLQWYQQKPG KAPKLLVHGASNLHRCVPSRFSCSGFHTTFSLTISGLQRDD FATYFCAVLEFFGPGTKVEIKRTVAAPSVFIFPPSDEQLKS | 6 |
| 12A21HC | SQHLVQSGTQVKKPGASVRVSCQASGYTFTNYILHWWRQAP GQGLEWMGLIKPVFGAVNYARQFQGRIQLTRDIYREIAFLD LSGLRSDDTAVYYCARDESGDDLKWHLHPWGQGTQVIVSPA STKG | 7 |
| 12a21kc | DIQMTQSPSSLSASVGDRVTINCQAGQGIGSSLNWYQKKPG RAPKLLVHGASNLQRGVPSRFSGSGFHTTFTLTISSLQPDD VATYFCAVFQWFGPGTKVDIKRTVAAPSVFIFPPSDEQLK | 8 |
| NIH-45-46HC | QVRLSQSGGQMKKPGESMRLSCRASGYEFLNCPINWIRLAP GRRPEWMGWLKPRGGAVNYARKFQGRVTMTRDVYSDTAFLE LRSLTSDDTAVYFCTRGKYCTARDYYNWDFEH | 9 |
| NIH-45-46kC | EIVLTQSPATLSLSPGETAIISCRTSQSGSLAWYQQRPGQA PRLVIYSGSTRAAGIPDRFSGSRWGADYNLSISNLESGDFG VYYCQQYEF | 10 |
| 8ANC131HC | QGQLVQSGGGLKKPGTSVTISCLASEYTFNEFVIHWIRQAP GQGPLWLGLIKRSGRLMTAYNFQDRLRLRRDRSIGTVFMEL RGLRPDDTAVYYCARDGLGEVAPDYRYGIDVWGQGSTVIVT AASTKG | 11 |
| 8ANC131KC | EIVLIQSPATLSLSPCERATLSCRASQGLNFVVWYQQKRGQ APRLLIHAPSGRAPGVPDRFSARGSGTEFSLVISSVEPDDF AIYYCQEYSSTPYNFGPGIRVDRKRTVAAPSVFIFPPSDEQ | 12 |
| 8ANC134HC | QGQLVQSGGGVKKPGTSVTISCLASEYTFNEFVIHWIRQAP GQGPVWLGLIKRSGRLMTSYKFQDRLSLRRDRSTGTVFMEL RGLRLDDTAVYYCARDGLGEVAPAYLYGIDAWGQGSTVIVT SASTKG | 13 |
| 8ANC134KC | EIVLTQSPATLSLSPGERATLSCRASQGLNFVVWYQQKGGQ APRLLIHGPTDRAPGVPDRFSARGSGTEFSLVISSVEPDDF ALYYCQEYSSTPYNFGPGIRVDRKRTVAAPSVFIFPPSDEQ | 14 |
| IB2530HC | QVQLEQSGTAVRKPGASVTLSCQASGYNFVKYIIHWVRQKP GLGFEWVGMIDPYRGRPWSAHKFQGRLSLSRDTSMEILYMT LTSLKSDDTATYFCARAEAASDSHSRPIMFDH | 15 |
| B2530KC | QVQLEQSGTAVRKPGASVTLSCQASGYNFVKYIIHWVRQKP GLGFEWVGMIDPYRGRPWSAHKFQGRLSLSRDTSMEILYMT LTSLKSDDTATYFCARAEAASDSHSRPIMFDH | 16 |
| INC9HC | QVQLEQSGTAVRKPGASVILSCQASGYNFVKYIIHWVRQKP GLGFEWVGMIDPYRGRPWSAHKFQGRLSLSRDTSMEILYMT LTSLKSDDTATYFCARAEAASDSHSRPIMFDH | 17 |
| INC9KC | QVQLEQSGTAVRKPGASVTLSCQASGYNFVKYIIHWVRQKP GLGFEWVGMIDPYRGRPWSAHKFQGRLSLSRDTSMEILYMT LTSLKSDDTATYFCARAEAASDSHSRPIMFDH | 18 |
| 8ANC195HC | QIHLVQSGTEVKKPGSSVTVSCKAYGVNTFGLYAVNWVRQA PGQSLEYIGQIWRWKSSASHHFRGRVLISAVDLTGSSPPIS SLEIKNLTSDDTAVYFCTTTSTYDKWSGLHHDGVMAFSSWG QGTLISVSAASTKG | 19 |
| 8ANC195KC | DIQMTQSPSTLAASIGGTVRVSCRASQSITGNWVAWYQQRP GKAPRLLIYRGAALLGGVPSRFSGSAAGTDFTLTIGNLQAE DFGTFYCQQYDTYPGTFGQGTKVEVKRTVAAPSVFIFPPSD EQ | 20 |

The heavy chain variable regions (IgH) and light chain variable regions (IgL) of additional antibodies are listed below, where the CDRs are in bold.

| IgH SEQUENCES | | |
|---|---|---|
| IMGT | Sequence | SEQ ID NO: |
| 10-1369 | QVQLQESGPGLVKPLETLSLTCNVSGAFIADHYWSWIRLPLGKGPEWIGYVHDSGDINYNPSLKNRVHLSLDKSTNQVSLKLMAVTAGDSALYYCATTKHGRRIYGVVAFGEWFTYFYMDVWGRGTTVTVSS | 21 |
| 10-259 | QVHLQESGPGLVKPSETLSLTCNVSGTLVRDNYWSWMRQPLGKQPEWIGYVHDSGDTNYNPSLKSRVHLSLDKSNNLVSLRLTAVTAADSATYYCATTKHGRRIYGIVAFNEWFTYFYMDVWGKGTTVTVSS | 22 |
| 10-303 | QVQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSS | 23 |
| 10-410 | QVQLQESGPGLVKPPETLSLTCSVSGASVNDAYWSWIRQSPGKRPEWVGYVHHSGDTNYNPSLKRRVTFSLDTAKNEVSLKLVALTAADSAVYFCARALHGKRIYGIVALGELFTYFYMDVWGKGTTVTVSS | 24 |
| 10-1130 | QVQLQESGPGLVKPPETLSLTCSVSGASINDAYWSWIRQSPGKRPEWVGYVHHSGDTNYNPSLKRRVTFSLDTAKNEVSLKLVDLTAADSAVYFCARALHGKRIYGIVALGELFTYFYMDVWGKGTTVTVSS | 25 |
| 10-1121 | QVQLQESGPGLVKPPETLSLTCSVSGASINDAYWSWIRQSPGKRPEWVGYVHHSGDTNYNPSLKRRVSFSLDTAKNEVSLKLVDLTAADSAIYFCARALHGKRIYGIVALGELFTYFYMDVWGKGTTVTVSS | 26 |
| 10-1146 | QVQLVESGPGLVTPSETLSLTCTVSNGSVSGRFWSWIRQSPGRGLEWIGYFSDTDRSEYSPSLRSRLTLSLDASRNQLSLKLKSVTAADSATYYCARAQQGKRIYGIVSFGEFFYYYYMDAWGKGTAVTVSS | 27 |
| 10-996 | QVQLQESGPGLVKPSETLSLTCSVSNGSVSGRFWSWIRQSPGRGLEWIGYFSDTEKSNYNPSLRSRLTLSVDASKNQLSLKLNSVTAADSATYYCARTQQGKRIYGVVSFGEFFHYYYMDAWGKGTAVTVSS | 28 |
| 10-1341 | QVQLQESGPGLVKPSETLSVTCSVSGDSMNNYYWTWIRQSPGKGLEWIGYISDRESATYNPSLNSRVVISRDTSTNQLSLKLNSVTPADTAVYYCATARRGQRIYGVVSFGEFFYYYSMDVWGRGTTVTVSS | 29 |
| 10-847 | QVQLQESGPGLVKPSETLSVTCSVSGDSMNNYYWTWIRQSPGKGLEWIGYISDRASATYNPSLNSRVVISRDTSKNQLSLKLNSVTPADTAVYYCATARRGQRIYGVVSFGEFFYYYSMDVWGKGTTVTVSS | 30 |
| 10-1074 | QVQLQESGPGLVKPSETLSVTCSVSGDSMNNYYWTWIRQSPGKGLEWIGYISDRESATYNPSLNSRVVISRDTSKNQLSLKLNSVTPADTAVYYCATARRGQRIYGVVSFGEFFYYYSMDVWGKGTTVTVSS | 31 |
| 10-1074GM | QVQLQESGPGLVKPSETLSVTCSVSGDSMNNSYWTWIRQSPGKGLEWIGYISKSESANYNPSLNSRVVISRDTSKNQLSLKLNSVTPADTAVYYCATARHGQRIYGVVSFGEFFTYYSMDVWGKGTTVTVSS | 32 |
| KABAT | Sequence | SEQ ID NO: |
| 10-1369 | QVQLQESGPGLVKPLETLSLTCNVSGAFIADHYWSWIRLPLGKGPEWIGYVHDSGDINYNPSLKNRVHLSLDKSTNQVSLKLMAVTAGDSALYYCATTKHGRRIYGVVAFGEWFTYFYMDVWGRGTTVTVSS | 21 |
| 10-259 | QVHLQESGPGLVKPSETLSLTCNVSGTLVRDNYWSWMRQPLGKQPEWIGYVHDSGDTNYNPSLKSRVHLSLDKSNNLVSLRLTAVTAADSATYYCATTKHGRRIYGIVAFNEWFTYFYMDVWGKGTTVTVSS | 22 |

-continued

| | | |
|---|---|---|
| 10-303 | QVQLQESGPGLVKPSETLSLTCSVSGASISDSYWSWIRRSP GKGLEWIGYVHKSGDTNYSPSLKSRVNLSLDTSKNQVSLSL VAATAADSGKYYCARTLHGRRIYGIVAFNEWFTYFYMDVWG NGTQVTVSS | 23 |
| 10-410 | QVQLQESGPGLVKPPETLSLTCSVSGASVNDAYWSWIRQSP GKRPEWVGYVHHSGDTNYNPSLKRRVIFSLDTAKNEVSLKL VALTAADSAVYFCARALHGKRIYGIVALGELFTYFYMDVWG KGTTVTVSS | 24 |
| 10-1130 | QVQLQESGPGLVKPPETLSLTCSVSGASINDAYWSWIRQSP GKRPEWVGYVHHSGDTNYNPSLKRRVITSLDTAKNEVSLKL VDLTAADSAVYFCARALHGKRIYGIVALGELFTYFYMDVWG KGTTVTVSS | 25 |
| 10-1121 | QVQLQESGPGLVKPPETLSLTCSVSGASINDAYWSWIRQSP GKRPEWVGYVHHSGDTNYNPSLKRRVSFSLDTAKNEVSLKL VDLTAADSAIYFCARALHGKRIYGIVALGELFTYFYMDVWG KGTTVTVSS | 26 |
| 10-1146 | QVQLVESGPGLVTPSETLSLTCTVSNGSVSGRFWSWIRQSP GRGLEWIGYFSDTDRSEYSPSLRSRLTLSLDASRNQLSLKL KSVTAADSATYYCARAQQGKRIYGIVSFGEFFYYYMDAWG KGTAVTVSS | 27 |
| 10-996 | QVQLQESGPGLVKPSETLSLTCSVSNGSVSGRFWSWIRQSP GRGLEWIGYFSDTEKSNYNPSLRSRLTLSVDASKNQLSLKL NSVTAADSATYYCARTQQGKRIYGVVSFGEFFHYYYMDAWG KGTAVTVSS | 28 |
| 10-1341 | QVQLQESGPGLVKPSETLSVTCSVSGDSMNNYYWTWIRQSP GKGLEWIGYISDRESATYNPSLNSRVVISRDTSTNQLSLKL NSVTPADTAVYYCATARRGQRIYGVVSFGEFFYYYSMDVWG RGTTVTVSS | 29 |
| 10-847 | QVQLQESGPGLVKPSETLSVTCSVSGDSMNNYYWTWIRQSP GKGLEWIGYISDRASATYNPSLNSRVVISRDTSKNQLSLKL NSVTPADTAVYYCATARRGQRIYGVVSFGEFFYYYSMDVWG KGTTVTVSS | 30 |
| 10-1074 | QVQLQESGPGLVKPSETLSVTCSVSGDSMNNYYWTWIRQSP GKGLEWIGYISDRESATYNPSLNSRVVISRDTSKNQLSLKL NSVTPADTAVYYCATARRGQRIYGVVSFGEFFYYYSMDVWG KGTTVTVSS | 31 |
| 10-1074GM | QVQLQESGPGLVKPSETLSVTCSVSGDSMNNSYWTWIRQSP GKGLEWIGYISKSESANYNPSLNSRVVISRDTSKNQLSLKL NSVTPADTAVYYCATARHGQRIYGVVSFGEFFTYYSMDVWG KGTTVTVSS | 32 |

| IgL SEQUENCES | | |
|---|---|---|
| IMGT | Sequence | SEQ ID NO: |
| 10-1369 | SSMSVSPGETAKITCGEKSIGSRAVQWYQKKPGQPPSLIIY NNQDRPSGVPERFSASPDIEFGTTATLTITNVEAGDEADYY CHIYDARRPTNWVFDRGTTLTVL | 33 |
| 10-259 | SSMSVSPGETAKISCGKESIGSRAVQWYQQKSGQPPSLIIY NNQDRPSGVPERFSATPDFGAGTTATLTITNVEADDEADYY CHIYDARGGTNWVFDRGATLTVL | 34 |
| 10-303 | SDISVAPGETARISCGEKSLGSRAVQWYQHRAGQAPSLIIY NNQDRPSGIPERFSGSPDSPFGTTATLTITSVEAGDEADYY CHIWDSRVPTKWVFGGGTTLTVL | 35 |
| 10-1121 | SFVSVAPGQTARITCGEESLGSRSVIWYQQRPGQAPSLIMY NNHDRPSGIPERFSGSPGSTFGTTATLTITSVEAGDEADYY CHIWDSRRPTNWVFGEGTTLTVL | 36 |
| 10-410 | SFVSVAPGQTARITCGEESLGSRSVIWYQQRPGQAPSLIIY NNNDRPSGIPERFSGSPGSTFGTTATLTITSVEAGDEADYY CHIWDSRRPTNWVFGEGTTLTVL | 37 |
| 10-1130 | SFVSVAPGQTARITCGEESLGSRSVIWYQQRPGQAPSLIIY NNNDRPSGIPERFSGSPGSTFGTTATLTITSVEAGDEADYY CHIWDSRRPTNWVFGEGTTLTVL | 38 |

-continued

| | Sequence | SEQ ID NO: |
|---|---|---|
| 10-847 | SYVRPLSVALGETASISCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 39 |
| 10-1074<br>and<br>10-1074GM | SYVRPLSVALGETARISCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 40 |
| 10-1341 | SYVRPLSVALGETARISCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 41 |
| 10-996 | SSLPLSVAPGATAKIACGEKSFASRAVQWYQQKPGQAPVLI<br>IYNNQDRPAGVSERFSGTPDVGFGSTATLTISRVEAGDEAD<br>YYCHKWDSRSPLSWVFGGGTQLTVL | 42 |
| 10-1146 | SSLPLSLAPGATAKIPCGEKSRGSRAVQWYQQKPGQAPTLI<br>IYNNQDRPAGVSERYSGNPDVAIGVTATLTISRVEAGDEAE<br>YYCHYWDSRSPISWVFGGWTQLTVL | 43 |

| KABAT | Sequence | SEQ ID NO: |
|---|---|---|
| 10-1369 | SSMSVSPGETAKITCGEKSIGSRAVQWYQKKPGQPPSLIIY<br>NNQDRPSGVPERFSASPDIEFGTTATLTITNVEAGDEADYY<br>CHIYDARRPTNWVFDRGTTLTVL | 33 |
| 10-259 | SSMSVSPGETAKISCGKESIGSRAVQWYQQKSGQPPSLIIY<br>NNQDRPSGVPERFSATPDFGAGTTATLTITNVEADDEADYY<br>CHIYDARGGTNWVFDRGATLTVL | 34 |
| 10-303 | SDISVAPGETARISCGEKSLGSRAVQWYQHRAGQAPSLIIY<br>NNQDRPSGIPERFSGSPDSPFGTTATLTITSVEAGDEADYY<br>CHIWDSRVPTKWVFGGGTTLTVL | 35 |
| 10-1121 | SFVSVAPGQTARITCGEESLGSRSVIWYQQRPGQAPSLIMY<br>NNHDRPSGIPERFSGSPGSTFGTTATLTITSVEAGDEADYY<br>CHIWDSRRPTNWVFGEGTTLTVL | 36 |
| 10-410 | SFVSVAPGQTARITCGEESLGSRSVIWYQQRPGQAPSLIIY<br>NNNDRPSGIPERFSGSPGSTFGTTATLTITSVEAGDEADYY<br>CHIWDSRRPTNWVFGEGTTLTVL | 37 |
| 10-1130 | SFVSVAPGQTARITCGEESLGSRSVIWYQQRPGQAPSLIIY<br>NNNDRPSGIPERFSGSPGSTFGTTATLTITSVEAGDEADYY<br>CHIWDSRRPTNWVFGEGTILTVL | 38 |
| 10-847 | SYVRPLSVALGETASISCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 39 |
| 10-1074<br>and<br>10-1074GM | SYVRPLSVALGETARTSCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 40 |
| 10-1341 | SYVRPLSVALGETARTSCGRQALGSRAVQWYQHRPGQAPIL<br>LIYNNQDRPSGIPERFSGTPDINFGTRATLTISGVEAGDEA<br>DYYCHMWDSRSGFSWSFGGATRLTVL | 41 |
| 10-996 | SSLPLSVAPGATAKIACGEKSFASRAVQWYQQKPGQAPVLI<br>IYNNQDRPAGVSERFSGTPDVGFGSTATLTISRVEAGDEAD<br>YYCHKWDSRSPLSWVFGGGTQLTVL | 42 |
| 10-1146 | SSLPLSLAPGATAKIPCGEKSRGSRAVQWYQQKPGQAPILI<br>IYNNQDRPAGVSERYSGNPDVAIGVTATLTISRVEAGDEAE<br>YYCHYWDSRSPISWVFGGWTQLTVL | 43 |

Shown below are the amino acid sequences of PG16 heavy chain and light chain:

PG16 Igγ1
(SEQ ID No: 54)
(T)*MGWSCIILFLVATATGVHS*QEQLVESGGGVVQPGGSLRLSCLASGF
TFHKYGMHWVRQAPGKGLEWVALISDDGMRKYHSDSMWGRVTISRDNSK
NTLYLQFSSLKVEDTAMFFCAREAGGPIWHDDVKYYDFNDGYYNYHYMD
VWGKGTTVTVSSASTKGPSVFPLAPSSKSTSGGTAALGCLVKDYFPEPV
IVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYR

-continued

VVSVLTVLHQDWLNGKEYKGKVSNKALPAPIEKTISKAKGQPREPQVYT

LPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

PG16 Igλ2

(SEQ ID No: 55)

(*T*)*MGWSCIILFLVATATGSVT*QSALTQPASVSGSPGQTITISCNGTSS

DVGGFDSVSWYQQSPGKAPKVMVFDVSHRPSGISNRFSGSKSGNTASLT

ISGLHIEDEGDYFCSSLTDRSHRIFGGGTKVTVLGQPKAAPSVTLFPPS

SEELQANKATLVCLISDFYPGAVTVAWKADSSPVKAGVETTTPSKQSNN

KYAASSYLSLTPEQWKSHRSYSCQVTHEGSTVEKTVAPTECS

Italic: leader peptides
Bold: variable domains
Underlined: constant domains

Like ART, bNAbs can completely suppress viremia in HIV-1 infected humanized mice (Klein et al., Nature, 2012. 492(7427): p. 118-22 and Horwitz et al., Proc Natl Acad Sci USA, 2013. 110(41): p. 16538-43) and in SHIV infected macaques (Barouch et al., Nature, 2013. 503(7475): p. 224-8 and Shingai et al., Nature, 2013. 503(7475): p. 277-80). Similar to humans, termination of bNAb or ART therapy in hu-mice and macaques results in robust viral rebound, indicating persistence of a functionally silent pool of cells harboring replication-competent virus. Moreover, the relative frequency of latent CD4$^+$ T cells as measured by ex vivo re-activation is similar in ART suppressed hu-mice and humans (Marsden et al., J Virol, 2012. 86(1): p. 339-47 and Denton et al., J Virol, 2012. 86(1): p. 630-4). Therefore, antibodies and ART contain HIV-1 infection in hu-mice but also produce a latent reservoir.

Unlike ART however, antibodies can engage the host immune system by virtue of their Fc effector domains (Nimmerjahn et al., Nat Rev Immunol, 2008. 8(1): p. 34-47) and thereby accelerate clearance of cell free virus (Igarashi et al., Nat Med, 1999. 5(2): p. 211-6), induce antibody dependent cytotoxicity to kill infected cells (Chung et al., Proc Natl Acad Sci USA, 2011. 108(18): p. 7505-10; Sun et al., J Virol, 2011. 85(14): p. 6906-12 Bonsignori et al., J Virol, 2012. 86(21): p. 11521-32; Jost et al., Annu Rev Immunol, 2013. 31: p. 163-94; Forthal et al., J Virol, 2001. 75(15): p. 6953-61 and Forthal et al., Curr Opin HIV AIDS, 2013. 8(5): p. 393-401) and produce immune complexes that activate dendritic cells to become potent antigen presenting cells (Dhodapkar et al., Proc Natl Acad Sci USA, 2005. 102(8): p. 2910-5). Finally, bNAbs can prevent cell-cell transmission of HIV-1 (Malbec et al., J Exp Med, 2013. 210(13): p. 2813-21 and Abela et al., PLoS Pathog, 2012. 8(4): p. e1002634), whereas ART's activity in this regard is still debated (Sigal et al., Nature, 2011. 477(7362): p. 95-8; Schiffner et al., Vaccine, 2013. 31(49): p. 5789-97; and Agosto et al., PLoS Pathog, 2014. 10(2): p. e1003982).

The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). Chimeric antibodies include antibodies having one or more human antigen binding sequences (for example, CDRs) and containing one or more sequences derived from a non-human antibody, for example, an FR or C region sequence. In addition, chimeric antibodies included herein are those comprising a human variable region antigen binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non-human amino acid residues often are referred to as "import" residues, which typically are taken from an "import" variable region. Humanization may be performed following the method of Winter and co-workers (see, for example, Jones et al., Nature 321:522-525 (1986); Reichmann et al., Nature 332:323-327 (1988); Verhoeyen et al., Science 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), where substantially less than an intact human variable region has been substituted by the corresponding sequence from a non-human species.

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870 for example. Such linear antibody fragments can be monospecific or bispecific.

In certain embodiments, antibodies of the described invention are bispecific or multispecific. Bispecific antibodies are antibodies that have binding specificities for at least two different epitopes. Exemplary bispecific antibodies can bind to two different epitopes of a single antigen. Other such antibodies can combine a first antigen binding site with a binding site for a second antigen. Alternatively, an anti-HIV arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the infected cell. Bispecific antibodies also can be used to localize cytotoxic agents to infected cells. Bispecific antibodies can be prepared as full length antibodies or antibody fragments (for example, F(ab')2 bispecific antibodies). See for example, WO 96/16673, U.S. Pat. No. 5,837,234, WO98/02463, U.S. Pat. No. 5,821,337, and Mouquet et al., Nature. 467, 591-5 (2010).

Methods for making bispecific antibodies are known in the art. Traditional production of full length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991) and see also; Mouquet et al., Nature. 467, 591-5 (2010). Techniques for generating bispecific antibodies from antibody fragments also have been described in the literature. For example, bispecific antibodies can be prepared using chemical linkage. See Brennan et al., Science, 229: 81 (1985).

Typically, the antibodies of described in the invention can be produced using conventional hybridoma technology or made recombinantly using vectors and methods available in the art. Human antibodies also can be generated by in vitro activated B cells (see, for example, U.S. Pat. Nos. 5,567,610 and 5,229,275). General methods in molecular genetics and genetic engineering useful in the present invention are described in the current editions of Molecular Cloning: A Laboratory Manual (Sambrook, et al., Molecular Cloning: A Laboratory Manual (Fourth Edition) Cold Spring Harbor Lab. press, 2012), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R.I. Freshney. 1987. Liss, Inc. New York, NY), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, Nature Biotechnology 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties of neutralizing multiple HIV-1 viral strains. As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function using the functional assays described herein.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

As disclosed herein, bNAbs are significantly more effective than ART in blocking the establishment of the reservoir when given early in the infection. One of the key differences between antibodies and ART is that antibodies can engage a variety of host immune effector pathways by way of their Fc receptors (Nimmerjahn et al., Nat Rev Immunol, 2008. 8(1): p. 34-47). Consistent with this important difference, the mechanism by which antibodies interfere with the establishment of the reservoir is dependent on their ability to bind to Fc receptors.

The terms "Fc receptor" or "FcR" are used to describe a receptor that binds to the Fc region of an antibody. An Fc receptor is a protein found on the surface of certain cells—including, among others, B lymphocytes, follicular dendritic cells, natural killer cells, macrophages, neutrophils, eosinophils, basophils and mast cells—that contribute to the protective functions of the immune system. Its name is derived from its binding specificity for the Fc region (fragment crystallizable region) of an antibody.

Several antibody functions are mediated by Fc receptors. For example, Fc receptors bind to antibodies that are attached to infected cells or invading pathogens. Their activity stimulates phagocytic or cytotoxic cells to destroy microbes, or infected cells by antibody-mediated phagocytosis or antibody-dependent cell-mediated cytotoxicity. It was also known in the art that the Fc region of an antibody ensures that each antibody generates an appropriate immune response for a given antigen, by binding to a specific class of Fc receptors, and other immune molecules, such as complement proteins. FcRs are defined by their specificity for immunoglobulin isotypes: Fc receptors for IgG antibodies are referred to as FcγR, for IgE as FcεR, for IgA as FcαR and so on. Surface receptors for immunoglobulin G are present in two distinct classes—those that activate cells upon their crosslinking ("activation FcRs") and those that inhibit activation upon co-engagement ("inhibitory FcRs").

In all mammalian species studied to date, four different classes of IgG Fc-receptors have been defined: FcγRI (CD64), FcγRII (CD32), FcγRIII (CDI6) and FcγIV. Whereas FcγRI displays high affinity for the antibody constant region and restricted isotype specificity, FcγRII and FcγRIII have low affinity for the Fc region of IgG but a broader isotype binding pattern (Ravetch and Kinet, 1991; Hulett and Hogarth, Adv Immunol 57, 1-127 (1994)). FcγRIV is a recently identified receptor, conserved in all mammalian species with intermediate affinity and restricted subclass specificity (Mechetina et al., Immunogenetics 54, 463-468 (2002); Davis et al., Immunol Rev 190, 123-136 (2002); Nimmerjahn et al., Immunity 23, 41-51 (2005)).

Functionally there are two different classes of Fc-receptors: the activation and the inhibitory receptors, which transmit their signals via immunoreceptor tyrosine based activation (ITAM) or inhibitory motifs (ITIM), respectively (Ravetch, in Fundamental Immunology W. E. Paul, Ed. (Lippincott-Raven, Philadelphia, (2003); Ravetch and Lanier, Science 290, 84-89 (2000). The paired expression of activating and inhibitory molecules on the same cell is the key for the generation of a balanced immune response. Additionally, it has been appreciated that the IgG Fc-receptors show significant differences in their affinity for individual antibody isotypes rendering certain isotypes more strictly regulated than others (Nimmerjahn et al., 2005).

In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, Annu Rev Immunol, 15, 203-234 (1997); FcRs are reviewed in Ravetch and Kinet, Annu Rev Immunol, 9, 457-92 (1991); Capel et al., Immunomethods, 4, 25-34 (1994); and de Haas et al, J Lab Clin Med, 126, 330-41 (1995), Nimmerjahn and Ravetch 2006, Ravetch Fc Receptors in Fundemental Immunology, ed William Paul 5th Ed. each of which is incorporated herein by reference).

As used herein, the term "Fc fragment" or "Fc region" is used to define a C-terminal region of an immunoglobulin heavy chain. Such an Fc region is the tail region of an antibody that interacts with Fc receptors and some proteins of the complement system. The Fc region may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. A native sequence Fc region comprises an amino acid sequence identical to the amino acid sequence of an Fc region found in nature. A variant Fc region as appreciated by one of ordinary skill in the art comprises an amino acid sequence which differs from that of a native sequence Fc region by virtue of at least one "amino acid modification."

In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment is important for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. See, e.g., US20080286819, US20100278808, US20100189714, US 2009004179, 20080206246, 20110150867, and WO2013095966, each of which is incorporated herein by reference.

As the Fc receptor function is involved in HIV-1 latent reservoir, the bNAb antibody of this invention can include antibody variable regions with the desired binding specificities (antibody-antigen combining sites) fused to immunoglobulin constant domain sequences. The fusion can be with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

C. Inducers

Some embodiments of this invention involve using viral transcription inducers. A transcription inducer refers to any agent that can induce the transcriptional activation of the HIV-1 promoter, or re-activate latent HIV-1 from the patient viral reservoir directly or indirectly (e.g., facilitating T cell activation by removing an inhibitory pathway). Examples of suitable transcription inducers include vorinostat, an HDAC inhibitor (Contreras et al., J Biol Chem, 2009. 284(11): p. 6782-9; Archin et al., AIDS Res Hum Retroviruses, 2009. 25(2): p. 207-12; and Archin et al., AIDS, 2009. 23(14): p. 1799-806), I-BET151, a BET bromodomain inhibitor (Boehm et al., Cell Cycle, 2013. 12(3): p. 452-62), and αCTLA4, a T-cell inhibitory pathway blocker (Alegre et al., Nat. Rev. Immunol. 2001. p. 220-228 and Krummel et al., J. Exp. Med. 1995. p. 459-465. See also US 20140128391. For example, the use of HDAC inhibitors in combination with the bNAbs of this invention can be used in disrupting, decreasing, or purging the latently infected reservoirs in patients, particularly patients undergoing Highly Active Antiretroviral Therapy (HAART).

Experiments with indicator cell lines indicate that HDAC and bromodomain inhibitors show synergy when combined with conventional transcriptional activators in re-activating HIV-1 in vitro. Consistent with the in vitro experiments, the combination of these inducers appears to be synergistic in vivo since single inducers had no measurable effect above the background controls, while ~57% of the hu-mice treated with antibodies plus combination inducers failed to rebound. Irrespective of the mechanism, the reservoir of HIV-1 infected cells remaining after combination inducer and antibody therapy in hu-mice is significantly decreased, establishing the principle that the HIV-1 reservoir can be altered by combination therapy with antibodies and inducers in vivo.

D. Other Anti-Retroviral Agents

The above-described antibodies and viral transcription inducers can used in combination with one or more antiretroviral agents for the treatment of HIV latency and/or infection. See, e.g., US 2010/0166806, US 2010/0324034, and US 2012/0203014, which are hereby incorporated in their entirety.

Compositions according to the present invention may also be administered in combination with other agents to enhance the biological activity of such agents. Such agents may include any one or more of the standard anti-HIV agents which are known in the art, including, but not limited to, azidothymidine (AZT), dideoxycytidine (ddC), and dideoxyinosine (ddI). Additional agents which have shown anti-HIV effects and may be combined with compositions in accordance to the invention include, for example, raltegravir, maraviroc, bestatin, human chorionic gonadotropin (hCG), levamisole, estrogen, efavirenz, etravirine, indomethacin, emtricitabine, tenofovir disoproxil fumarate, amprenavir, tipranavir, indinavir, ritonavir, darunavir, enfuvirtide, and gramicidin.

E. Treatment Compositions and Methods

In one embodiment, the present invention provides a composition comprising at least one bNAb mentioned above alone or in combination with one of the other active agent mentioned above and a pharmaceutically acceptable carrier. The composition may include a plurality of the antibodies having the characteristics described herein in any combination and can further include antibodies neutralizing to HIV as are known in the art.

It is to be understood that compositions can be a single or a combination of antibodies disclosed herein, which can be the same or different, in order to prophylactically or therapeutically treat the progression of various subtypes of HIV infection. When an antibody or active agent is administered to an animal or a human, it can be combined with one or more pharmaceutically acceptable carriers, excipients or adjuvants as are known to one of ordinary skilled in the art.

Further, with respect to determining the effective level in a patient for treatment of HIV, in particular, suitable animal models are available and have been widely implemented for evaluating the in vivo efficacy against HIV of various therapy protocols. These models include mice, monkeys and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection).

According to another embodiment, the present invention provides an antibody-based pharmaceutical composition comprising an effective amount of an isolated bNAb of the invention, or an affinity matured version, which provides a prophylactic or therapeutic treatment choice to reduce the latent reservoir and infection of the HIV virus. The pharmaceutical compositions of the present invention may be formulated by any number of strategies known in the art (e.g., see McGoff and Scher, 2000, Solution Formulation of Proteins/Peptides: In McNally, E. J., ed. Protein Formulation and Delivery. New York, NY: Marcel Dekker; pp. 139-158; Akers and Defilippis, 2000, Peptides and Proteins as Parenteral Solutions. In: Pharmaceutical Formulation Development of Peptides and Proteins. Philadelphia, PA: Talyor and Francis; pp. 145-177; Akers, et al., 2002, Pharm. Biotechnol. 14:47-127). A pharmaceutically acceptable composition suitable for patient administration will contain an effective amount of the bNAb antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody or other active agent to a concentration which provides the desired beneficial palliative or curative results while at the same time minimizing any adverse side effects that might occur from too high a concentration. It may also have a preservative effect. Thus, for an active ingredient having a high physiological activity, more of the excipient will be employed. On the other hand, for any active ingredient(s) that exhibit a lower physiological activity, a lesser quantity of the excipient will be employed.

The above described bNAb antibodies and antibody compositions, comprising at least one or a combination of the antibodies described herein, can be administered for the prophylactic and therapeutic treatment of HIV viral infection.

The composition can be a pharmaceutical composition that contains a pharmaceutically acceptable carrier. The term "pharmaceutical composition" refers to the combination of an active agent with a carrier, inert or active, making the composition especially suitable for diagnostic or therapeutic use in vivo or ex vivo. A "carrier" as used herein includes pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN.; polyethylene glycol (PEG), and PLURONICS.

The term "pharmaceutically acceptable carrier" refers to any of the standard pharmaceutical carriers, such as a phosphate buffered saline solution, water, emulsions, and various types of wetting agents. The compositions also can include stabilizers and preservatives. A pharmaceutically acceptable carrier, after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active agent. Examples of other carriers include colloidal silicon oxide, magnesium stearate, cellulose, and sodium lauryl sulfate.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model (such as non-human primates). A subject to be treated can be identified by standard diagnosing techniques for the disorder.

According to another embodiment, the present invention provides a method of reducing or preventing the establishment of a latent reservoir of HIV infected cells in a subject in need thereof (e.g., a subject infected with HIV or at risk of infection with HIV), thereby treating infection with a HIV infection, comprising administering to the subject a pharmaceutical composition comprising the HIV antibodies disclosed herein. The compositions of the invention can include more than one antibody having the characteristics disclosed (for example, a plurality or pool of antibodies). It also can include other HIV neutralizing antibodies and/or active agent known in the art.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody of the invention. When used for in vivo therapy, the antibodies of the invention are administered to the patient in therapeutically effective amounts (i.e., amounts that eliminate or reduce the patient's latent viral reservoir). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the antibodies may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 10 mg/ml.

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Other therapeutic regimens may be combined with the administration of the bNAb HIV antibody of the present invention. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The parameters for assessing successful treatment and improvement in the disease are also readily measurable by routine procedures familiar to a physician.

The terms "treating" or "treatment" or "alleviation" are used interchangeably and refer to both therapeutic treatment and prophylactic or preventative measures; wherein the object is to prevent or slow down (lessen) the targeted pathologic condition or disorder. In particular, it refers to administration of a compound or agent to a subject, who has a disorder (such as an HIV infection), with the purpose to cure, alleviate, relieve, remedy, delay the onset of, prevent, or ameliorate the disorder, the symptom of the disorder, the disease state secondary to the disorder, or the predisposition toward the disorder.

Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

Eliminating the HIV-1 reservoir in chronic infection is key to curing the disease, but direct measurement of the latent reservoir to evaluate therapeutic eradication strategies remains difficult (Siliciano et al., Curr Opin HIV AIDS, 2013. 8(4): p. 318-25). Quantitative viral outgrowth assays and PCR-based assays of integrated DNA yield variable results (Eriksson et al., PLoS Pathog, 2013. 9(2): p. e1003174) in part because PCR cannot distinguish between inactive and permanently disabled proviruses, and outgrowth assays underestimate reservoir size (Ho et al., Cell, 2013. 155(3): p. 540-51). To that end, the most effective way to evaluate the reservoir in vivo is to measure viral rebound after terminating therapy as disclosed in the examples below.

The terms "prevent," "preventing," "prevention," "prophylactic treatment" and the like refer to reducing the probability of developing a disorder or condition in a subject, who does not have, but is at risk of or susceptible to developing a disorder or condition.

A "therapeutically effective amount" refers to the amount of an agent sufficient to effect beneficial or desired results. A therapeutically effective amount can be administered in one or more administrations, applications or dosages and is not intended to be limited to a particular formulation or administration route.

Administration "in combination with" one or more further therapeutic agents includes simultaneous (concurrent) and consecutive administration in any order.

Pharmaceutically effective compositions of this invention may be administered to humans and other animals by a variety of methods that may include continuous or intermittent administration. Examples of methods of administration may include, but are not limited to, oral, rectal, parenteral, intracisternal, intrasternal, intravaginal, intraperitoneal, topical, transdermal, buccal, or as an oral or nasal spray. Accordingly, the pharmaceutically effective compositions may also include pharmaceutically acceptable additives, carriers or excipients. Such pharmaceutical compositions may also include the active ingredients formulated together with one or more non-toxic, pharmaceutically acceptable carriers specially formulated for oral administration in solid or liquid form, for parenteral injection or for rectal administration according to standard methods known in the art.

The term "parenteral" administration refers to modes of administration which include intravenous, intramuscular, intraperitoneal, intracisternal, intrasternal, subcutaneous and intraarticular injection and infusion. Injectable mixtures are known in the art and comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof.

F. Kits

Another aspect of the invention provides kits. In general, kits according to the present invention comprise an isolated anti-HIV bNAb antibody, a first viral transcription inducer, and a second viral transcription inducer. Components of the kits can be provided in containers. The containers are provided in packaged combination in a suitable package, such as a box made of cardboard, glass, plastic, metal, or a combination thereof. Suitable packaging materials for pharmaceutical compositions or reagents are known and widely used in the art, and thus need not be specified herein.

The kits of the invention can comprise any number of additional reagents or substances that are useful for practicing a method of the invention. Such substances include, but are not limited to: reagents (including buffers) for detecting HIV virus or components thereof or HIV-infected cells in a subject. The kits of the invention can be provided at any temperature. For example, for storage of kits containing protein-based agents, it is preferred that they are provided and maintained below 0° C., preferably at or below −20° C., or otherwise in a frozen state.

The kit may further comprise a software package for data analysis of the physiological status of a subject to be treated, which may include reference profiles for comparison with the relevant test profile. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

EXAMPLES

Example 1 Materials and Methods

This example describes materials and methods used in Examples 2-5 below.

Mice

NOD Rag1$^{-/-}$Il2rg$^{NULL}$ (NOD.Cg-Rag$^{tm1Mom}$ Il2rg$^{tm1wj1}$/SzJ, NRG) mice were purchased from The Jackson Laboratory. All mice were bred and maintained at the Comparative Bioscience Center of The Rockefeller University according to guidelines established by the Institutional Animal Committee. All experiments were performed with authorization from the Institutional Review Board and the IACUC at The Rockefeller University.

Humanized Mice

Humanized mice were generated as previously described in Klein et al., Nature, 2012. 492(7427): p. 118-22. Briefly, human fetal livers were obtained from Advanced Bioscience Resources (ABR). Fetal livers were homogenized and incubated in HBSS media with 0.1% collagenase IV (Sigma-Aldrich), 40 mM HEPES, 2 mM CaCl$_2$) and 2 U ml$^{-1}$ DNAase I (Roche) for 30 minutes at 37° C. Hematopoietic Stem Cells (HSCs) were isolated from digested liver using CD34$^+$ HSC isolation kit (Stem Cell Technologies). Neonatal NRG mice (1-5 days old) were sublethally irradiated with 100 cG and injected intrahepatically with 2×10$^5$ human CD34$^+$ HSCs 6 h after irradiation.

Mouse Screening for Humanization

Eight or more weeks after HSC injection, mice were screened for the presence of human lymphocytes in peripheral blood by flow cytometry. 200 µl whole blood was collected by facial vein bleed and peripheral blood mononuclear cells (PBMCs) were isolated by density gradient centrifugation using Ficoll-Paque Plus (GE Healthcare Life Sciences). PBMCs were stained with antibodies to mouse CD45-PECy7, human CD45-Pacific Orange, human CD3-Pacific Blue, human CD19-APC, human CD4-PE, human CD8-FITC, and human CD16-Alexa700 for 25 min at 4° C. Cells were washed and fixed using Cytofix/Cytoperm (BD Biosciences). Flow cytometry analysis was performed with a LSRFortessa (BD) and FlowJo software (Tree Star). For each mouse, the percentage of human lymphocytes [(100× human CD45$^+$)/(human CD45$^+$+mouse CD45$^+$)], termed huCD45$^+$%, and the percentage of human CD4$^+$ T cells (100×human CD45$^+$ CD3$^+$ CD4$^+$/human CD45$^+$), termed huCD4$^+$%, was calculated. Mice with at least 10% huCD45$^+$ and 10% huCD4$^+$ were selected for post-exposure prophylaxis experiments, and infected with two doses of HIV-1$_{YU2}$ (150 ng p24) by i.p. injections, 24 hours apart. Pre-treatment viremia was measured at 72-96 hours following the first HIV-1$_{YU2}$ injection, and treatment was initiated 4 days following the first injection. For experiments assessing the effects of bNAbs and inducers on established infections, mice with measurable human CD4$^+$ cells by FACS were injected with two doses of HIV-1$_{YU2}$ (150 ng), and pre-treatment viremia was measured 14-18 days after the first injection. Mice with plasma viral loads >3000 RNA copies/ml were selected to receive antibody therapy. After five subcutaneous antibody injections (see below), post-treatment viremias were measured. Only mice with completely suppressed plasma viremias were selected for further analysis and to receive viral inducers.

Plasma Viral Load Measurements 300-500 µl of whole blood was collected from mice at each time point by facial vein bleed. Whole blood was spun at 300 g for 10 minutes to separate plasma from the cellular fraction. Total RNA was extracted from 100 µl plasma using QIAmp MinElute Virus Spin Kit (Qiagen) in combination with RNase-free DNase (Qiagen), eluted in a 50 µl volume. HIV-1 RNA was quantified by qRT-PCR. The reaction mixture was prepared using TaqMan RNA-to-Ct 1-Step kit (Applied Biosystems), with 20 µl of eluted RNA, and a sequence specific probe targeting a conserved region of the HIV-1 pol gene (/HEX/5'-CCCACCAACARGCRGCCT TAACTG-3'/ZenDQ, HXB2 nt 4603 to 4626, SEQ ID No: 44) (Integrated DNA Technologies). Forward and reverse primer sequences were 5'-TAATGGCAGCAATTTCACCA-3' (HXB2 nt 4577-4596, SEQ ID No: 45) and 5'-GAATGC-CAAATTCCTGCTTGA-3' (HXB2 nt 4633 to 4653, SEQ ID No: 46), respectively. Cycle threshold (Ct) values were calibrated using standard samples with known amounts of absolute viral RNA copies. The quantitation limit was previously determined to be 800 copies/ml (Klein et al., Nature, 2012. 492(7427): p. 118-22).

Gp120 Sequencing

Gp120 cloning and sequencing was performed as previously described (Klein et al., 2012, HIV therapy by a combination of broadly neutralizing antibodies in humanized mice. In Nature (Nature Publishing Group), pp. 118-122). Briefly, cDNA was synthesized from viral RNA using SuperScript III reverse transcriptase (Invitrogen Life Technologies). cDNA was amplified with Expand Long Template PCR System (Roche) with nested PCR. Primers for the first round of PCR were 5'-GGCTTAGGCATCTCC-TATGGCAGGAAGAA-3' and 5'-GGTGTGTAGTTCTGC-CAATCAGGGAAGWAGCCTTGTG-3' (SEQ ID Nos: 47 and 48). Primers for the second round of PCR were 5'-TAGAAAGAGCAGAAGACAGTGGCAATGA-3' and 5'-TCATCAATGGTGGTGATGATGATGTTTTTCTCTC-TGCACCACTCTTCT-3'(SEQ ID Nos: 49 and 50). Gel-purified PCR amplicons were ligated into pCR4-TOPO (Invitrogen) and transformed into One Shot TOP10 cells. Individual colonies were sequenced using M13F and M13R primers. Sequences were aligned to gp120$_{YU2}$ (accession number M93258) and analyzed for mutations using Los Alamos Highlighter tool (hiv.lanl.gov/content/sequence/HIGHLIGHT/HIGHLIGHT_XYPLOT/highlighter.html).

Cell-Associated HIV-1 RNA

The cellular fraction of whole blood was resuspended in 400 μl PBS and PBMCs were isolated by density gradient centrifugation as described above. Lymphocytes were split into two samples, one for cell-associated HIV-1 RNA measurements, and one for cell-associated HIV-1 DNA measurements. Cell-associated RNA was extracted and quantified by the same procedures as described above for plasma viral RNA. The lower limit of detection was determined to be 10 copies viral RNA per qRT-PCR reaction. Cell-associated HIV-1 RNA is reported as the ratio of HIV-1 RNA copies per sample to CCR5 genomic DNA copies per equivalent sample measured in DNA extract. For terminal point measurements, spleen tissue was isolated, homogenized, and filtered through 40 μm mesh. Splenocytes were used to isolate HIV-1 RNA as described above.

Cell-Associated HIV-1 DNA

PBMCs were isolated from whole blood as described above. Splenocytes were isolated from spleen as described above. Total DNA was extracted using QIAmp DNA Blood Mini Kit (Qiagen) and eluted in 80 μl volume. Purified DNA was quantified for HIV-1 DNA by qPCR using the primers and probe for HIV-1 RNA quantification mentioned above. Genomic human CCR5 DNA was quantified with primers 5'-GTTGGACCAAGCTATGCAGGT-3' (forward, SEQ ID No: 51) and 5'-AGAAGCGTTTGGCAATGTGC-3' (reverse, SEQ ID No: 52), and the sequence-specific probe /HEX/5'-TTGGGATGACGCACTGCTGCATCAACCC-CA-3'/ZenDQ (SEQ ID No: 53). All qPCR reactions contained 25 μl AmpliTaq Gold PCR master mix (Applied Biosystems), in 50 μl reaction volume. Reaction mixtures were as previously described (Horwitz et al., Proc Natl Acad Sci USA, 2013. 110(41): p. 16538-43). HIV-1 DNA is reported as copies per sample to CCR5 genomic copies per equivalent sample.

Terminal Graft

The presence of human lymphocytes at the terminal point was quantified from the spleen and PBMCs by flow cytometry. Isolation of PBMCs and splenocytes were as described above. Staining procedures were as described above.

Antibody Concentrations

Plasma levels of passively administered antibodies were quantified by two independent methods. gp120-specific ELISA was as previously described (Klein et al., Nature, 2012. 492(7427): p. 118-22), using 10-1074 and 3BNC117 monoclonal antibodies as standard controls. The detection limit was 0.05 μg/ml. Because PG16 does not bind gp120, and endogenously produced gp120-reactive antibodies could confound the ELISA measurement, plasma antibody levels were also quantified by TZM-bl neutralization using the Tier 2 envelopes 3301.v1.c24 and YU2. A mixture with known amounts of 3BNC117, 10-1074, and PG16 was used as standard for calibration.

Day of Viral Rebound and Antibody Level at Rebound

Plasma viremias immediately preceding and following viral rebound were plotted on a semi-log-y-axis versus days post initial antibody injection (x-axis) for each individual mouse. The linear portion of viremia was fit to a line by least-squares linear regression. The day that viremia crossed the 800 copies/ml quantitation limit, termed rebound day, was calculated from the viremia fit. The antibody concentrations (as determined by TZM-bl neutralization) spanning before and after viral rebound were plotted on a semi-log-y-axis versus days post initial antibody injection. The linear portion of antibody concentrations was fit to a line by least-squares linear regression, and the antibody concentration on the rebound day was calculated from the fit.

Anti-Retroviral Therapy

Individual tablets of tenofovir disproxil-fumarate (TDF; Gilead Sciences), emtricitabine (FTC; Gilead Sciences), and raltegravir (RAL; Merck) were crushed into fine powder and manufactured with TestDiet 5B1Q feed (Modified LabDiet 5058 with 0.12% amoxicillin) into ½" irradiated pellets. Final concentrations of ART drugs in the food were 720 mg/kg TFV, 520 mg/kg FTC, and 4800 mg/kg RAL. Doses were chosen based on suppression of viremia in humanized mice as previously published (Denton et al., J Virol, 2012. 86(1): p. 630-4 and Nischang et al., PLoS ONE 2012. p. e38853), and by pharmacokinetic analysis of these drugs in humanized mice (unpublished, Speck Laboratory). To test potential toxicity, or reduced preference for drug-supplemented food, mice were weighed daily on normal diet, then switched to ART feed and weighed daily. There were no visible signs of toxicity and mice maintained their weights. Assuming mice weigh 25 grams and eat 4 grams of food per day, the drug doses correspond to 2.88 mg/kg TFV, 83 mg/kg FTC, and 768 mg/kg RAL daily.

Antibody Therapy

Plasmids encoding 10-1074 or PG16 heavy- and light-chain Ig genes were transfected into HEK 293E cells. Antibodies were isolated from tissue-culture supernatant using Protein G Sepharose 4 Fast-Flow (GE Healthcare). Antibodies were then buffer-exchanged into PBS and sterile-filtered using Ultrafree-CL centrifugal filters (0.22 μm; Millipore). Endotoxin was removed from antibody preparations using Triton X-114 (Sigma-Aldrich) as previously described (Aida et al., J Immunol Methods, 1990. 132(2): p. 191-5), and antibodies were concentrated to 10 mg/ml. Sterile, endotoxin-free 3BNC117 (20 mg/ml) was obtained from CellDex Therapeutics. All antibodies were injected subcutaneously as described.

Inducers

Vorinostat (Selleckchem) was suspended in sterile water or sterile water plus 0.5% methylcellulose, 0.1% Tween (v/v) and administered by oral gavage at doses of 60 mg/kg (Krejsgaard et al., 2010 Experimental dermatology 19, 1096-1102). For each mouse, three total doses were administered, spaced 48 hours apart. 100 μg doses of αCTLA4 were injected intraperitoneally (i.p.). Three total doses were administered, spaced 48 hours apart. I-BET was obtained from GlaxoSmithKline and dissolved in 10% beta-cyclo-dextrin, 5% DMSO in 0.9% saline and injected daily for 14 days at doses of 30 mg/kg (Dawson et al., 2011 Nature 478, 529-533.).

Statistical Analysis

Statistical analyses were performed using GraphPad Prism 6.0 for Mac OS X.

Example 2 Post Exposure Prophylaxis with bNAbs

The ART-resistant reservoir is established early in infection as evidenced by post-exposure prophylaxis experiments in humans and macaques. Post-exposure prophylaxis with ART or previous-generation bNAbs is only effective when administered within 24 hours of intravenous exposure. (Lifson et al., *Journal of Virology* 2000. p. 2584-2593; Wade et al., N Engl J Med, 1998. 339(20): p. 1409-14; Tsai, et al., Journal of Virology 1998. p. 4265; Tsai et al., *Science* 1995. p. 1-3; Landovitz et al., in *N Engl J Med* 2009. p. 1-8; Nishimura et al., Proc Natl Acad Sci USA, 2003. 100(25): p. 15131-6; and Ferrantelli et al., Virology, 2007. 358(1): p. 69-78). To determine if the current generation of more potent bNAbs can abort the establishment of a latent HIV-1 reservoir at later time points, post-exposure prophylaxis experiments were performed in humanized mice (FIG. 1A).

Figure 1B:
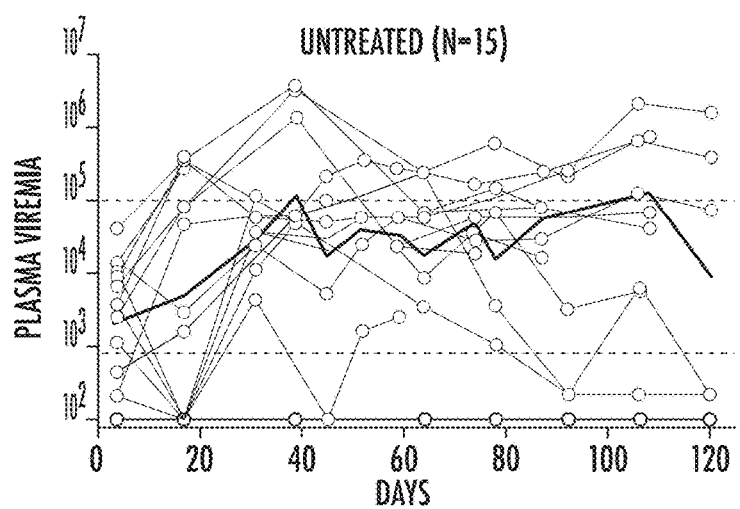

Mice were infected with HIV-1$_{YU2}$ (150 ng) by intraperitoneal injection, and treated with either ART (raltegravir, emtricitabine, tenofovir) (Denton et al., J Virol, 2012. 86(1): p. 630-4 and Nischang et al., *PLoS ONE* 2012. p. e38853) or a tri-mix of bNAbs (3BNC117, 10-1074, and PG16) (Horwitz et al., Proc Natl Acad Sci USA, 2013. 110(41): p. 16538-43) 4 or 8 days after infection when viremia was already detectable in 51 of 70 mice. Plasma viremia varied from undetectable to $2.70 \times 10^6$ viral RNA copies/ml at 4 days after infection (FIGS. 1B-E and 6). In the absence of therapy, 14 out of 15 mice in the control group developed sustained plasma viremia ranging from $2.48 \times 10^3$ to $4.19 \times 10^6$ copies/ml (FIG. 1B).

Figure 1C:
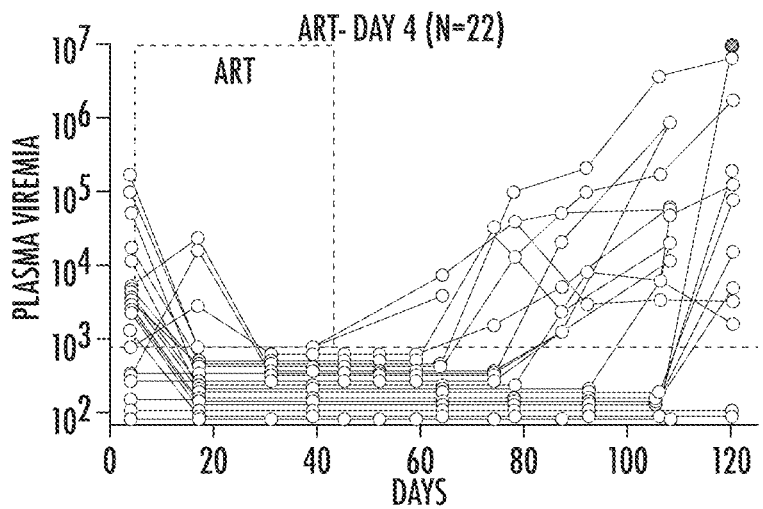
Figure 1D:
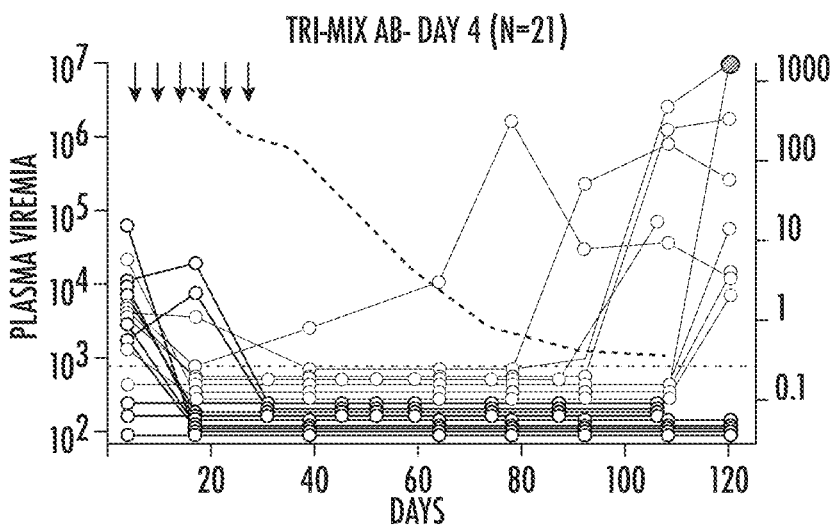
Figure 1E:
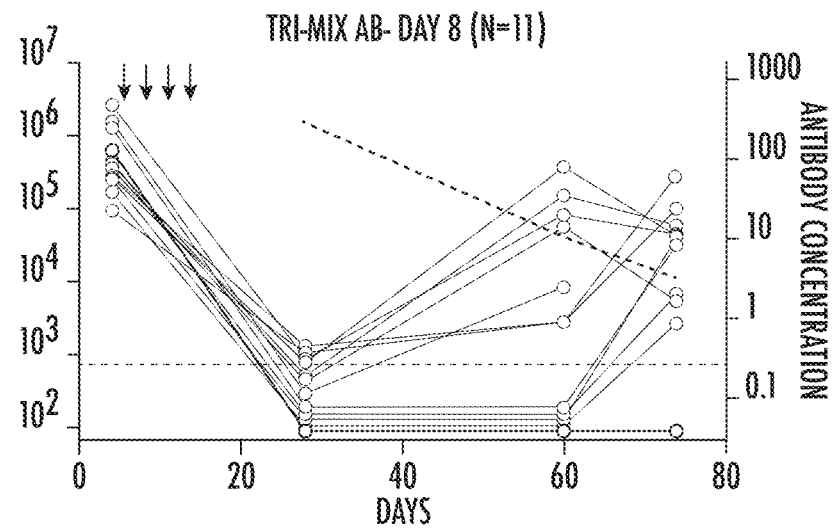
Figure 6A:
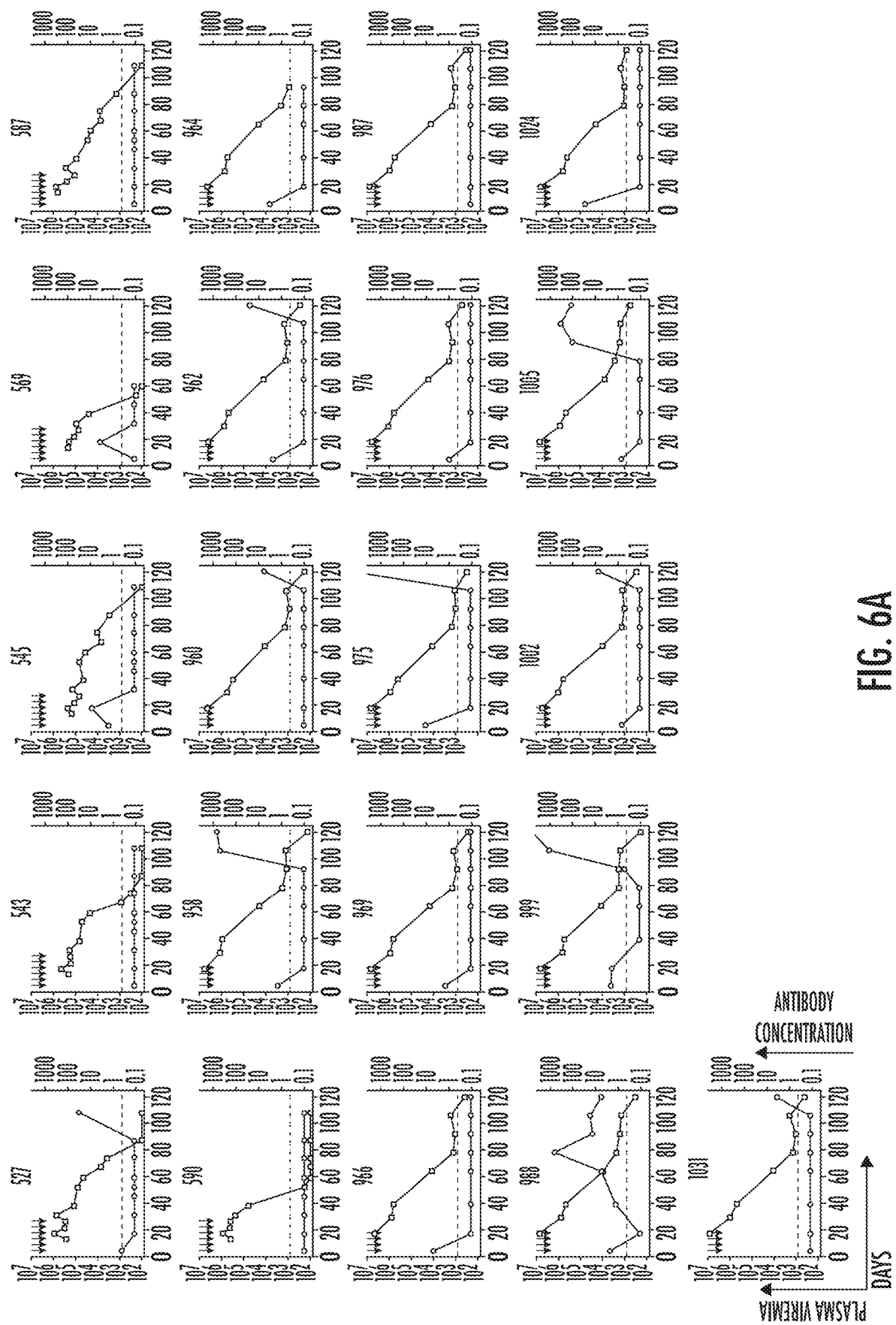
FIG. 6A and FIG. 6B are set of diagrams showing viremia and antibody levels in individual mice (bNAb Post-exposure prophylaxis) as in FIG. 1D.
Figure 6B:
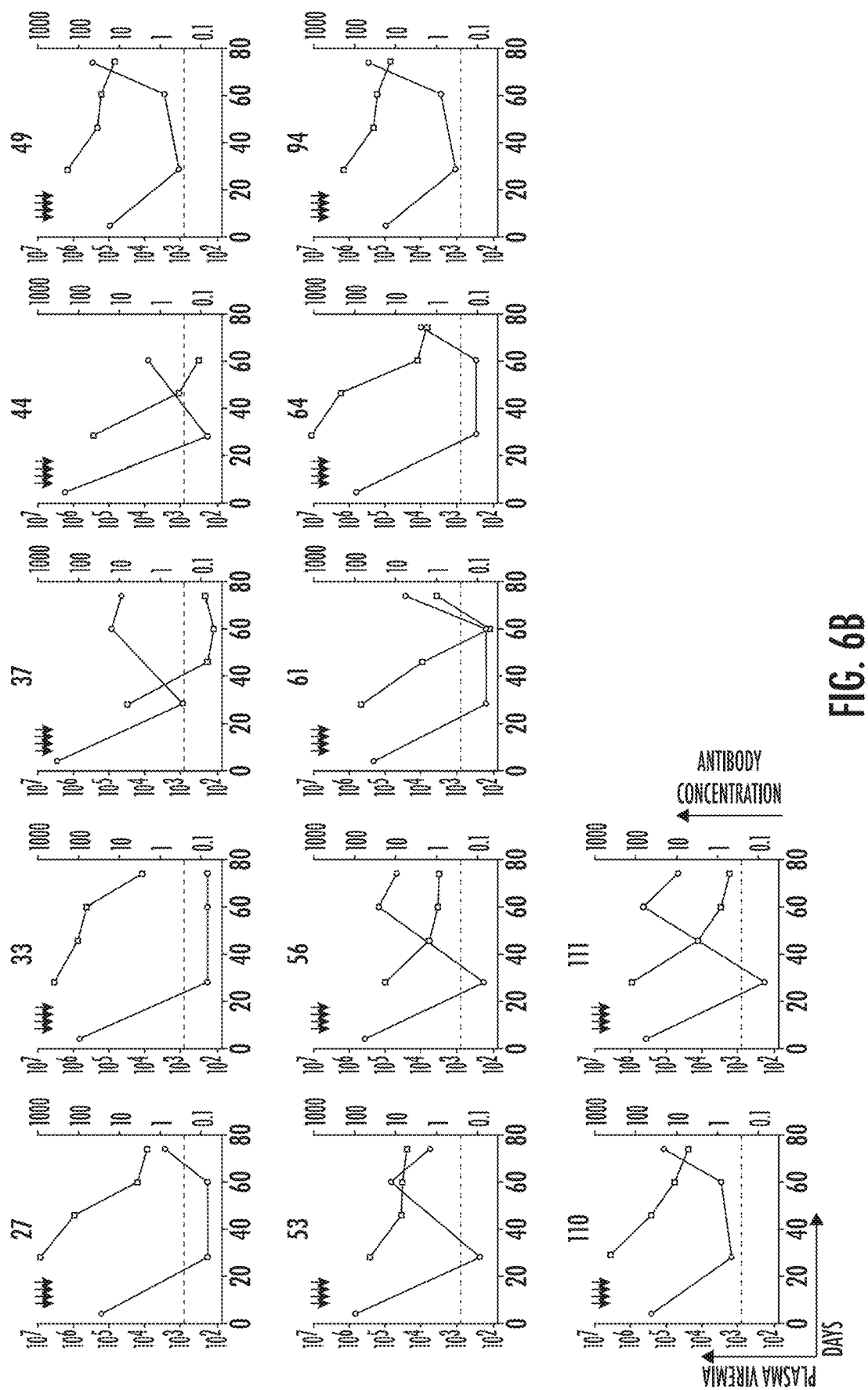

Doses of ART and antibodies were chosen on the basis of their therapeutic efficacy in chronic HIV-1 infection in hu-mice (Klein et al., Nature, 2012. 492(7427): p. 118-22; Horwitz et al., Proc Natl Acad Sci USA, 2013. 110(41): p. 16538-43; Denton et al., J Virol, 2012. 86(1): p. 630-4; and Nischang et al., *PLoS ONE* 2012. p. e38853). ART was administered in the food for 32-39 days starting 4 days after infection (Denton et al., J Virol, 2012. 86(1): p. 630-4; and Nischang et al., *PLoS ONE* 2012. p. e38853). Antibodies were administered subcutaneously with a loading dose of 3 mg per mouse, and 3-5 subsequent doses of 1.5 mg each, spaced 3-4 days apart (FIG. 1A). Consistent with human and macaque studies, 18 of 22 mice treated with ART showed viremia after ART termination, demonstrating that this form of therapy is relatively ineffective at preventing reservoir development in hu-mice when administered 4 days after infection (FIG. 1C). Among the 18 viremic mice, viremia was first detected 28 to 84 days after ART termination (FIGS. 1C and 6). In contrast, 10 of 21 hu-mice treated with antibodies 4 days after infection showed viremia by the terminal point (p=0.027), and for 9 of these 10 viremic mice, the first detectable viremia occurred 74-107 days after the last antibody injection (FIGS. 1D and 6). However, bNAb treatment after 8 days was far less effective, resulting in viremia in 10 of the 11 treated mice 44-58 days after the last antibody injection (FIG. 1E).

Figure 1F:
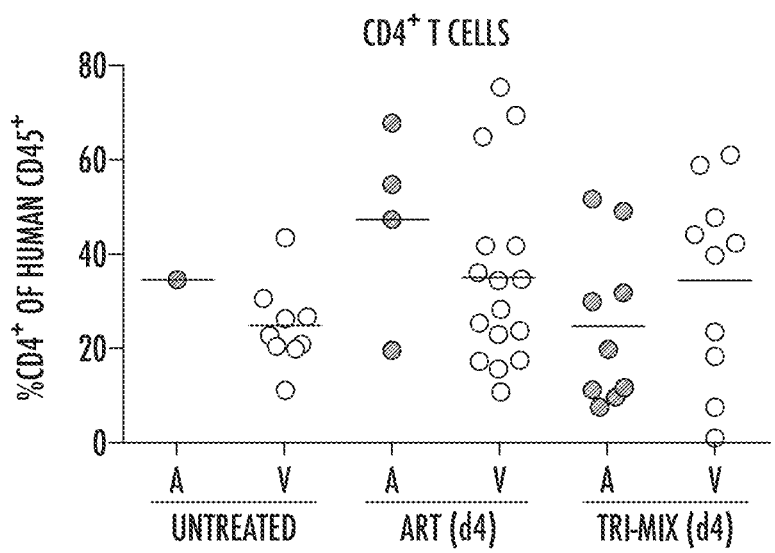
Figure 1G:
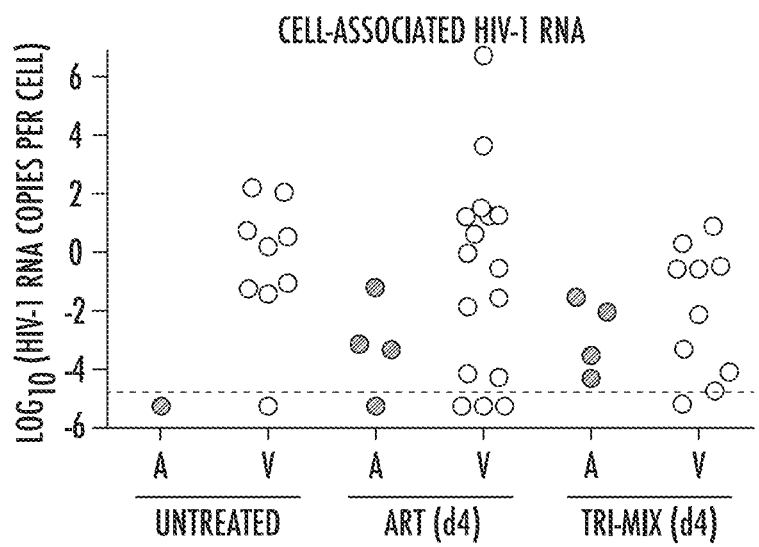

Mice in the early treatment group that failed to show detectable plasma viremia were further examined for the presence of human CD4$^+$ T cells and cell-associated HIV-1 RNA and DNA in the spleen. It was found that mice that failed to develop sustained plasma viremia showed CD4$^+$ T cell levels that were similar to infected controls. Therefore differences in CD4$^+$ T cell levels are unlikely to account for the observed differences between viremic and aviremic mice (FIG. 1F). Moreover, T cell-associated HIV-1 RNA levels were consistent with plasma viral loads, with mice that remained aviremic having either undetectable or lower cell-associated HIV-1 RNA than mice that developed sustained viremia (FIG. 1G).

Figure 1H:
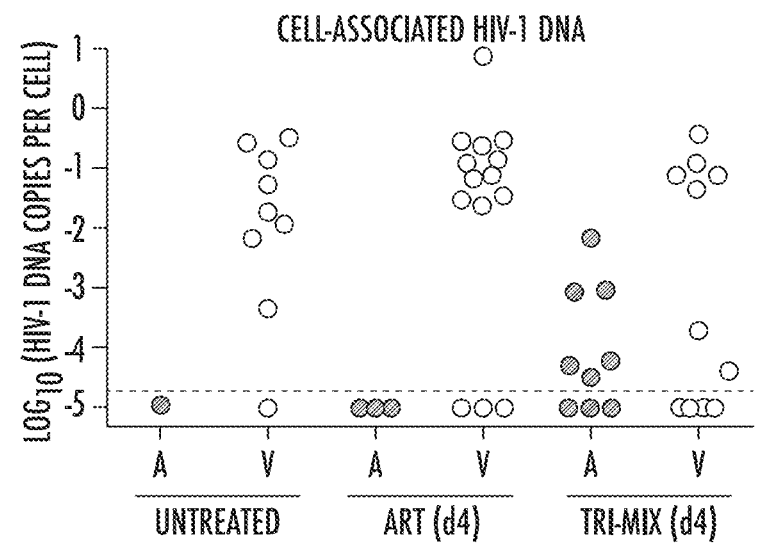

Cell-associated viral DNA was measured as an imperfect surrogate of the HIV-1 reservoir. HIV-1 DNA is thought to overestimate the reservoir because it fails to exclude damaged or incomplete viral sequences that cannot be reactivated. In addition, the overall number cells assayed in mice is limited and therefore the assay is not very sensitive. Nevertheless HIV-1 DNA measurements were found to be consistent with each mouse's rebound status (FIG. 1H). It was concluded that bNAbs can interfere with the establishment of the latent HIV-1 reservoir in hu-mice.

The above results indicate that bNAbs differ from ART in that they can prevent establishment of the latent HIV-1 reservoir in hu-mice at a time when ART is significantly less effective.

Example 3 Fc Receptor Binding is Required for bNAb Activity

Figure 7:
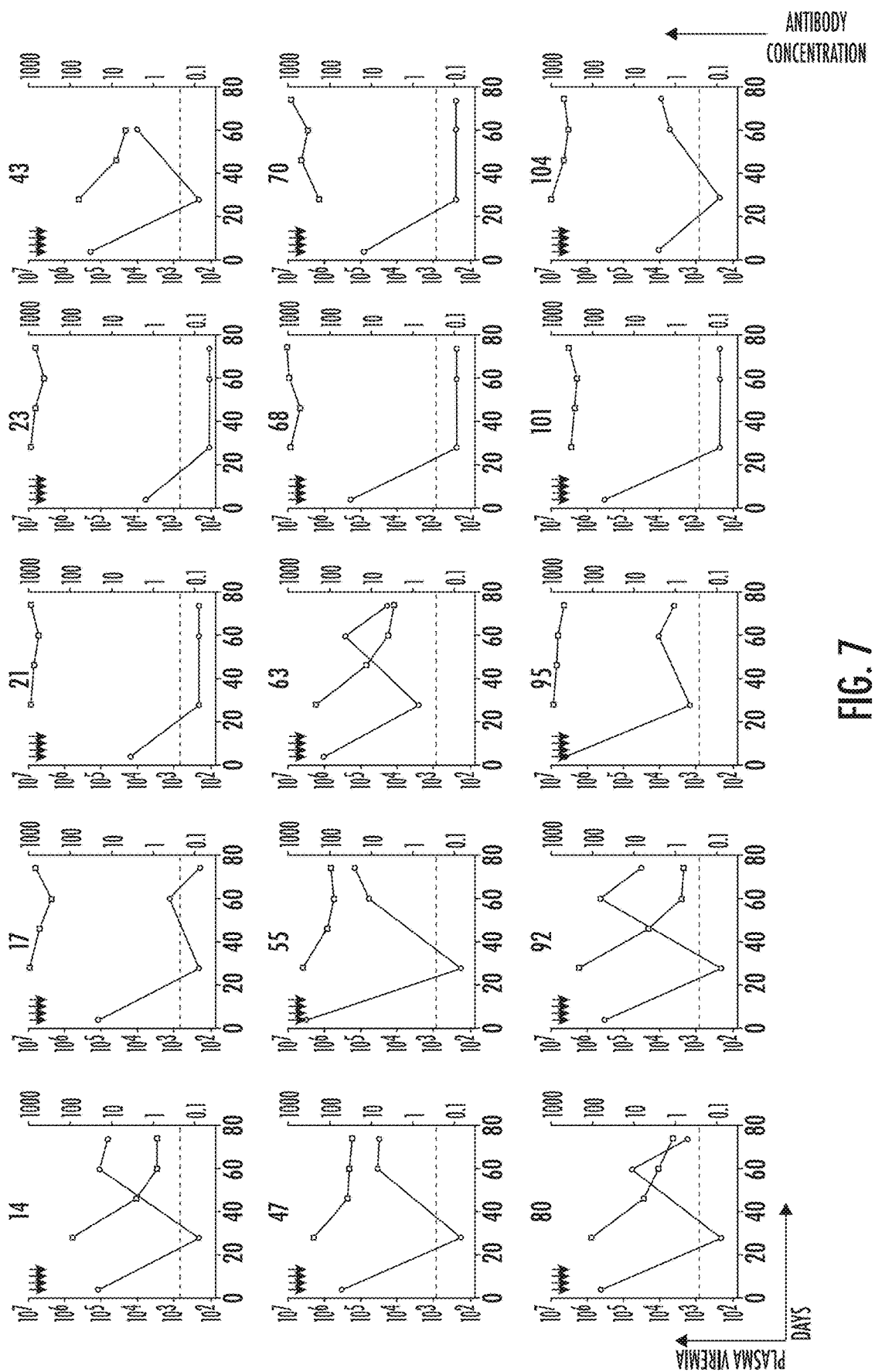
FIG. 7 is a set of diagram showing viremia and antibody levels in individual mice (FcR$^{null}$ tri-mix Post-exposure prophylaxis) as in FIG. 1D. Each mouse shown in FIG. 2A is shown individually.

To determine if the efficacy of bNAbs is dependent on the antibodies' ability to engage components of the immune system through their Fc domains, the day 4 post-exposure prophylaxis experiments were repeated using the same tri-mix of bNAbs carrying Fc region mutations that abrogate both human and mouse Fc-receptor binding (G236R/L328R; GRLR, herein referred to as FcR$^{null}$) (Horton et al., 2010, Blood 116, 3004-3012). Despite equivalent neutralizing activity in TZM-bl assays (Pietzsch et al., Proc Natl Acad Sci USA, 2012. 109(39), FcR$^{null}$ antibodies were far less potent than controls in vivo (FIGS. 2 and 7). Mice treated with FcR$^{null}$ tri-mix initially suppressed viremia at the same rate as the wild type antibody-treated mice (FIG. 2A). However 9 of 15 mice receiving post exposure prophylaxis with the FcR$^{null}$ tri-mix showed viral rebound by 44 days after the last antibody injection. In contrast, 44 days after the last injection of control antibodies, only 1 of 21 mice showed rebound viremia (p=0.0004). The loss of in vivo activity of the FcR$^{null}$ tri-mix was not due to lower antibody levels in the FcR$^{null}$ injected mice. In fact, antibody levels at the time of viral rebound were ~50-fold higher for mice receiving FcR$^{null}$ tri-mix compared to wild-type tri-mix (p=0.0035, FIG. 2C). It was concluded that effective post-exposure prophylaxis by bNAbs requires engagement of Fc-receptors.

The escape variants to the individual bNAbs in the tri-mix used in these experiments have been documented extensively (Horwitz et al., Proc Natl Acad Sci USA, 2013. 110(41): p. 16538-43, and Klein et al., Nature, 2012. 492 (7427): p. 118-22). However, inventors have never observed HIV-1 escape by mutation to the bNAb tri-mix. Rather viral rebound is usually due to a drop in antibody concentrations to sub-therapeutic levels (Horwitz et al., Proc Natl Acad Sci USA, 2013. 110(41): p. 16538-43, and Klein et al., Nature, 2012. 492(7427): p. 118-22). Because mice receiving FcR$^{null}$ tri-mix showed viral rebound in the presence of antibody concentrations far higher than the therapeutic threshold for wild-type antibodies (FIG. 2C), gp120 from 9 of the rebounding mice were cloned and sequenced to examine the mechanism for viral breakthrough in the presence of FcR$^{null}$ tri-mix (FIG. 2D). Among all 40 clones sequenced, not a single clone had the triple combination of signature mutations that confer escape to the antibody-trimix. It was concluded that viral rebound in FcR$^{null}$ tri-mix treated mice is not attributable to antibody escape, but rather reduced antibody potency. Thus, FcR$^{null}$ mutant antibodies, which cannot engage Fc receptors, are less active in suppressing infection than their wild type counterparts.

These results indicate that effective post-exposure prophylaxis by bNAbs requires engagement of Fc-receptors.

Example 4 Combination Therapy with bNAbs and Inducers

Figure 3A:
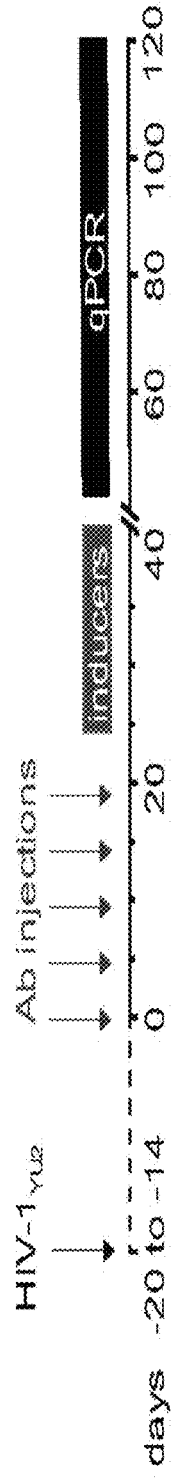
FIG. 3A, FIG. 3B, FIG. 3C, FIG. 3D, and FIG. 3E are a set of diagrams showing rebound viremia after therapy with single inducers.

A small number (~15%) of chronically infected hu-mice and macaques treated with antibodies fail to show rebound viremia after therapy is discontinued (Barouch et al., Nature, 2013. 503(7475): p. 224-8; Horwitz et al., Proc Natl Acad Sci USA, 2013. 110(41): p. 16538-43; Klein et al., Nature 2012, p. 118-122; and Shingai et al., Nature, 2013. 503 (7475): p. 277-80). This suggests that antibodies may be able to decrease the size of the reservoir, or interfere with its maintenance, in established infections. To determine whether agents that induce viral transcription from latently infected cells can enhance this effect antibody therapy was combined with viral inducers (FIGS. 3A and 8).

Hu-mice with established HIV-1$_{YU2}$ infections (viremia ranging from 4.70×10$^3$-7.96×10$^5$ copies/ml at 2-3 weeks after infection, FIGS. 3B-E) were treated with tri-mix bNAbs. When plasma viremia dropped below detection, they were co-administered a viral inducer for 5-14 days, and monitored for viral rebound for an additional 47-85 days. The inducers tested were vorinostat, an HDAC inhibitor (Archin et al., AIDS Res Hum Retroviruses, 2009. 25(2): p. 207-12; Archin et al., AIDS, 2009. 23(14): p. 1799-806; and Contreras et al., J Biol Chem, 2009. 284(11): p. 6782-9), I-BET 151, a BET protein inhibitor (Boehm et al., Cell Cycle, 2013. 12(3): p. 452-62), and αCTLA4, a T-cell inhibitory pathway blocker (Alegre et al., Nat. Rev. Immunol 2001. p. 220-228, and Krummel et al., J. Exp. Med. 1995. p. 459-465). They were selected because of their documented abilities to induce HIV-1 transcription in vitro, as well as their safety and established pharmacokinetic properties in mice (Krejsgaard et al., Exp Dermatol, 2010. 19(12): p. 1096-102; Kwon et al., Proc Natl Acad Sci USA, 1997. 94(15): p. 8099-103; and Nicodeme et al., Nature, 2010. 468(7327): p. 1119-23).

Figure 3B:
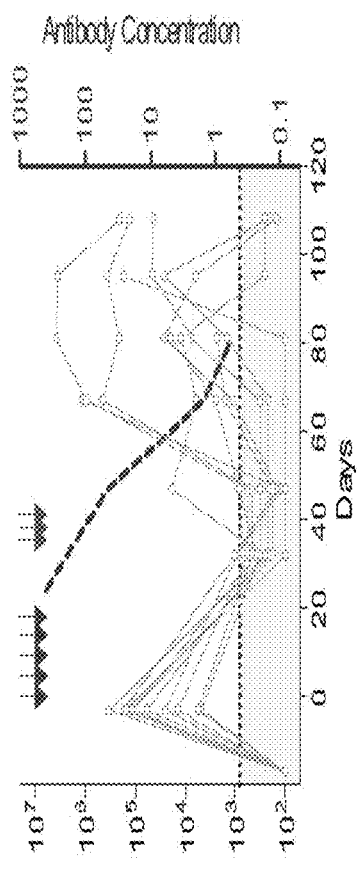
Figure 3C:
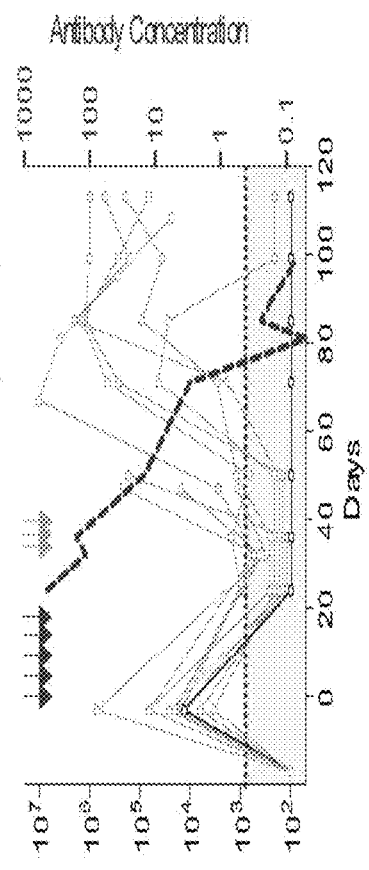
Figure 3D:
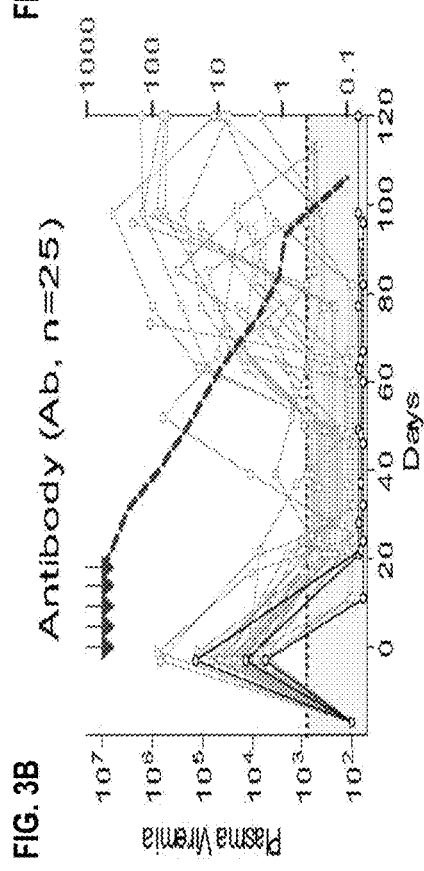
Figure 3E:
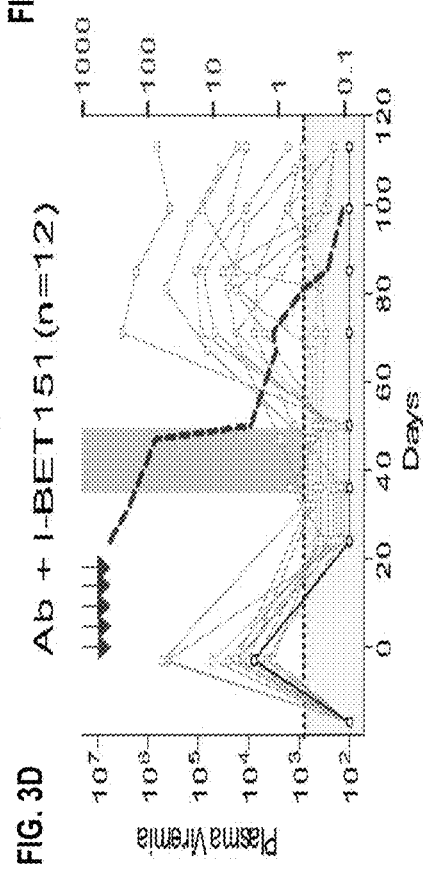
Figure 8B:
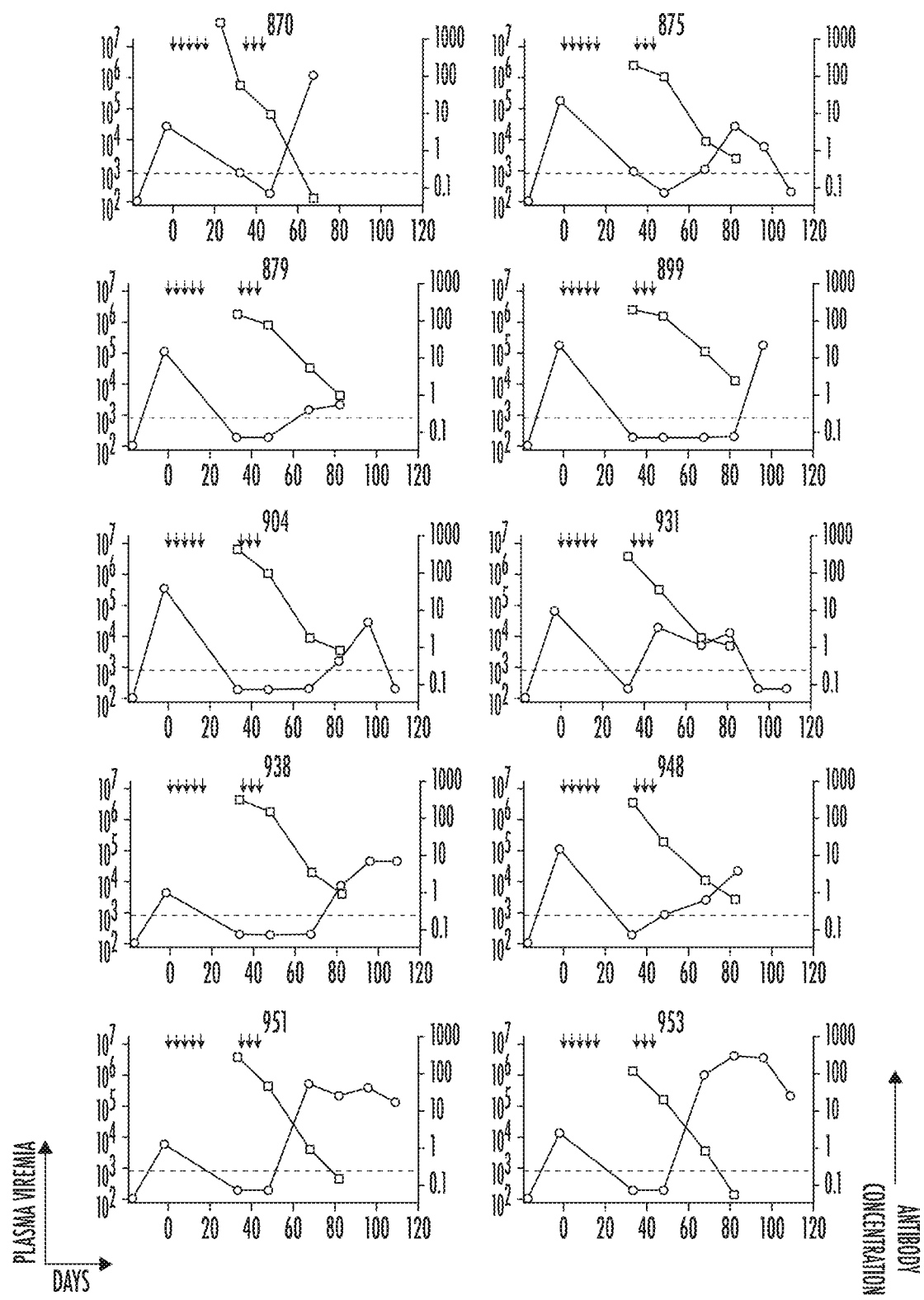
Figure 8C:
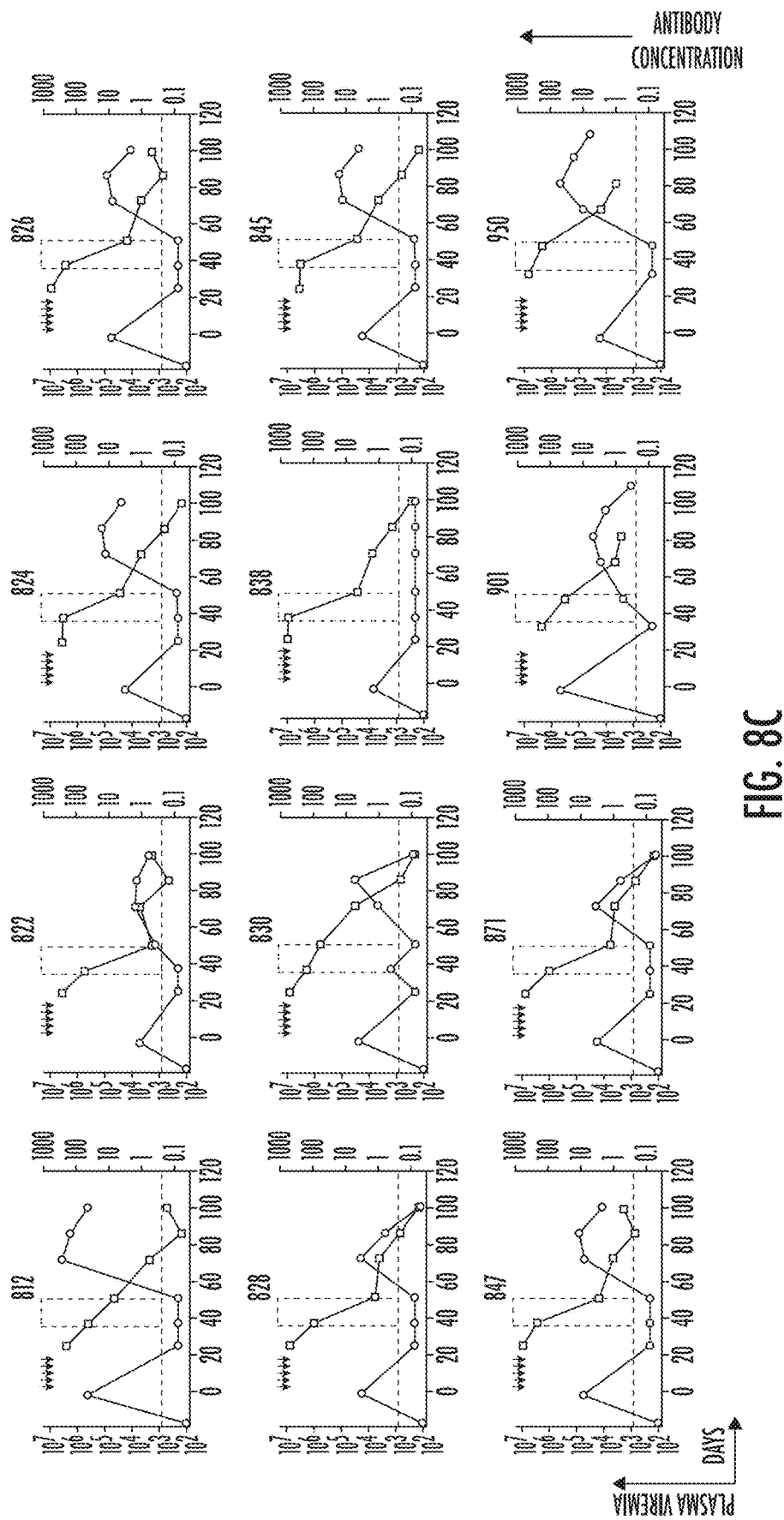
Figure 8D:
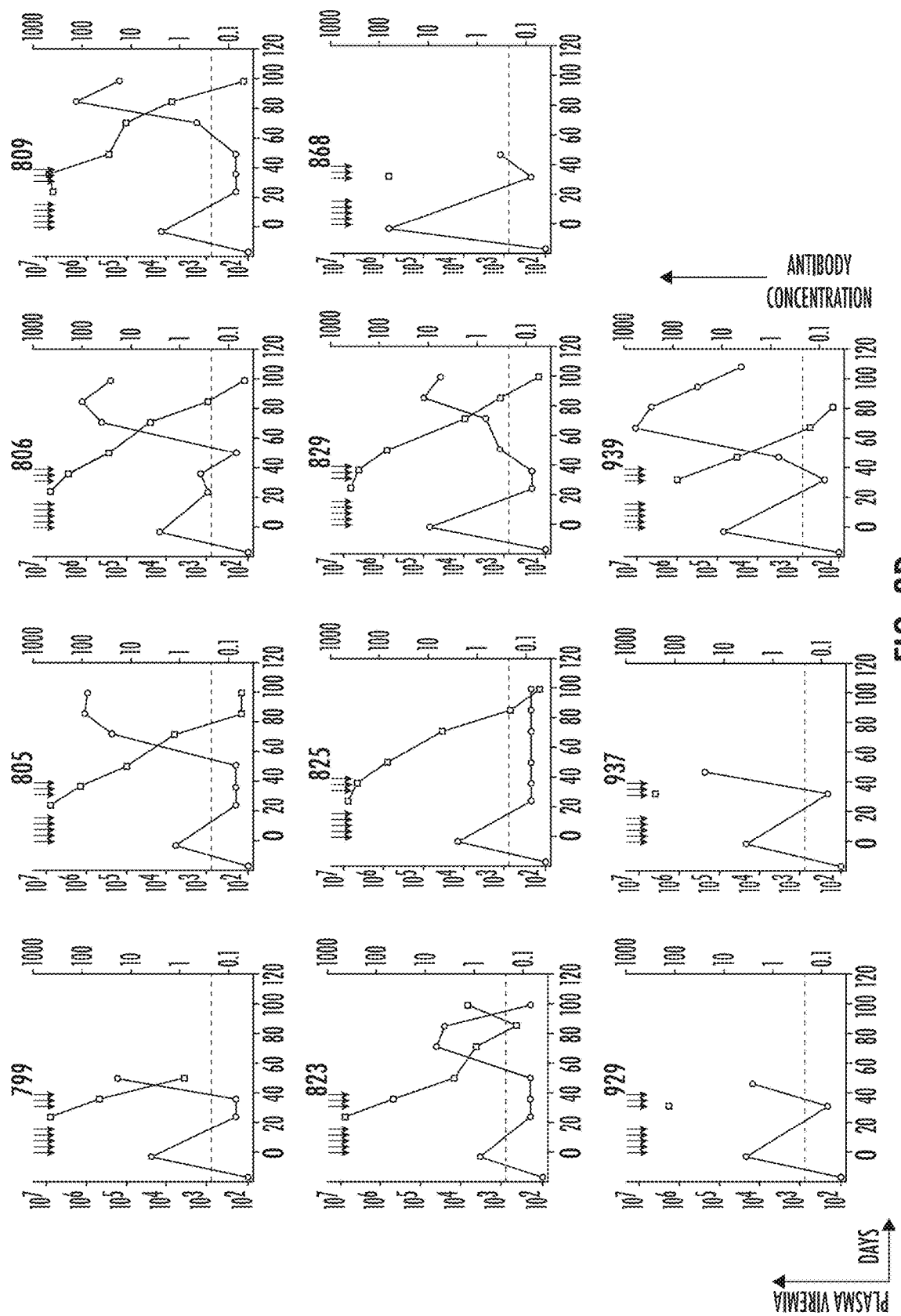
Figure 9:
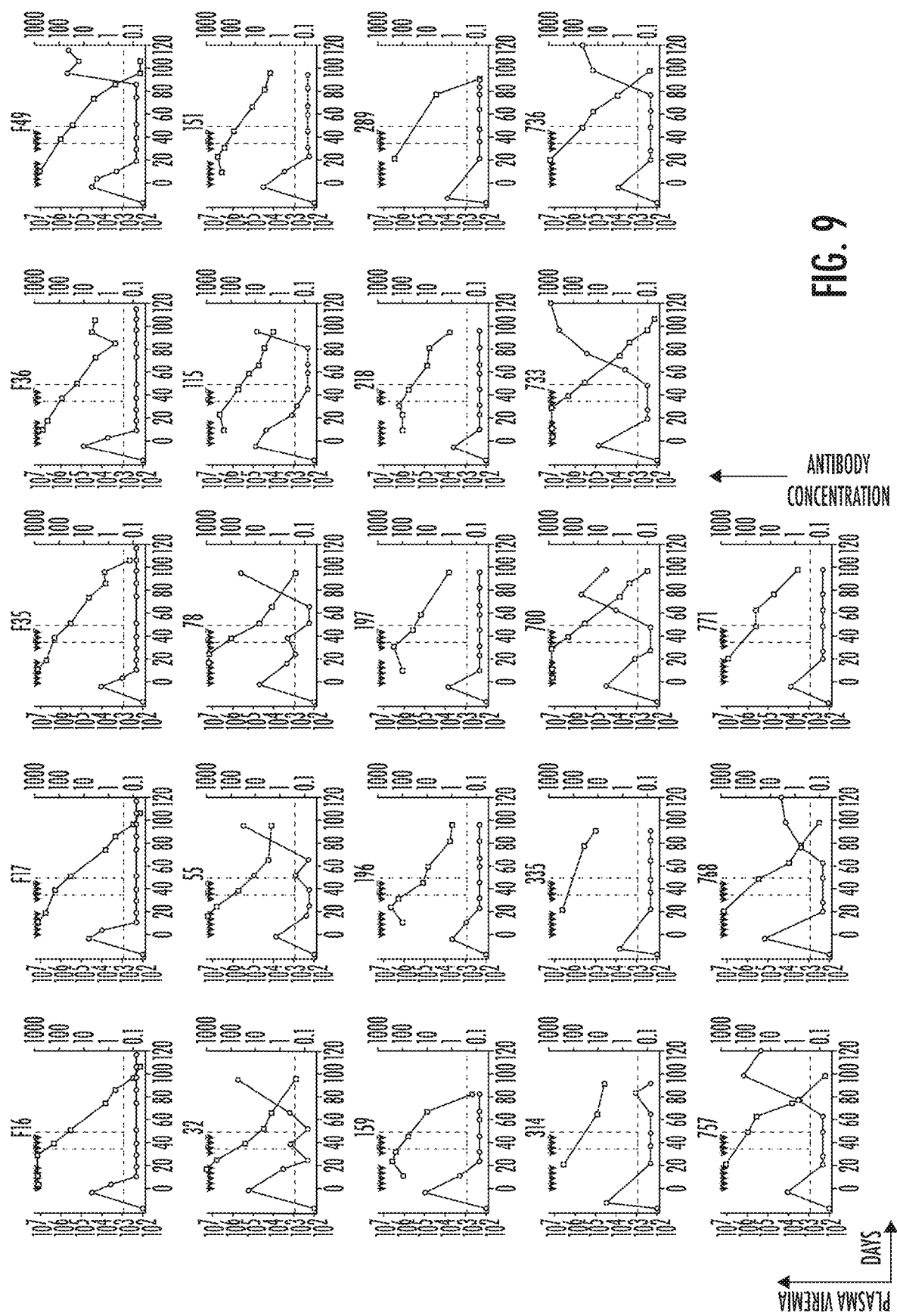
FIG. 9 is a set of diagram showing viremia in individual mice (antibody plus combination inducers) as in FIG. 4A. Each mouse shown in FIG. 4A is shown individually.
Figure 10A:
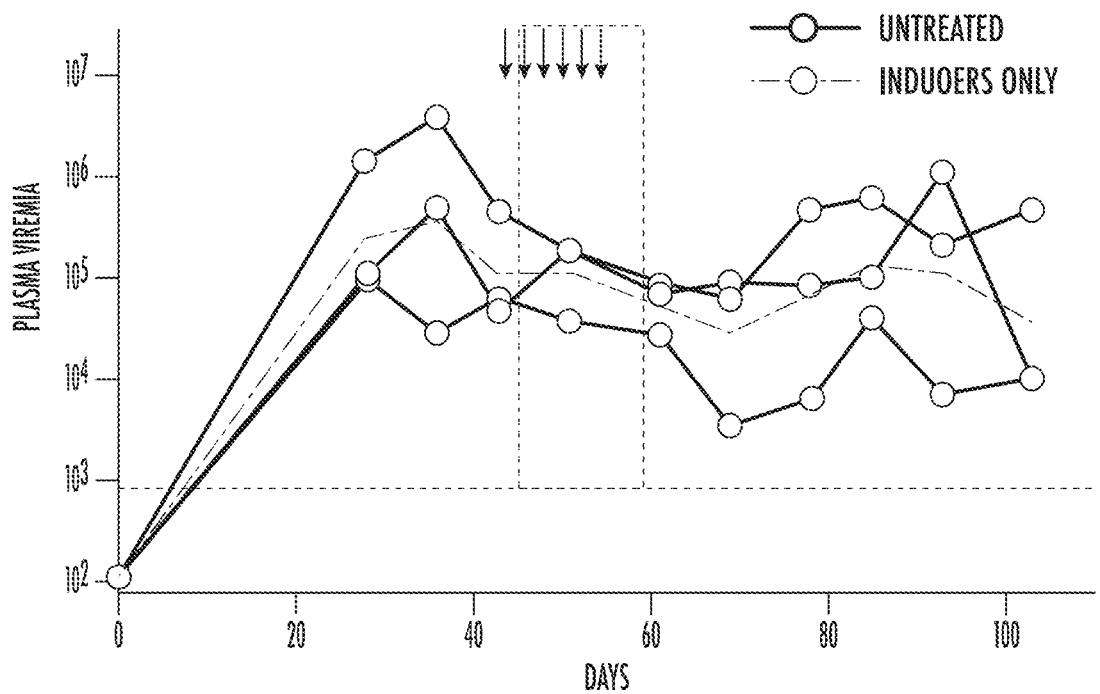
FIG. 10A, FIG. 10B, and FIG. 10C are a set of diagram showing sustained viremia in inducers treated mice without therapy.
Figure 10B:
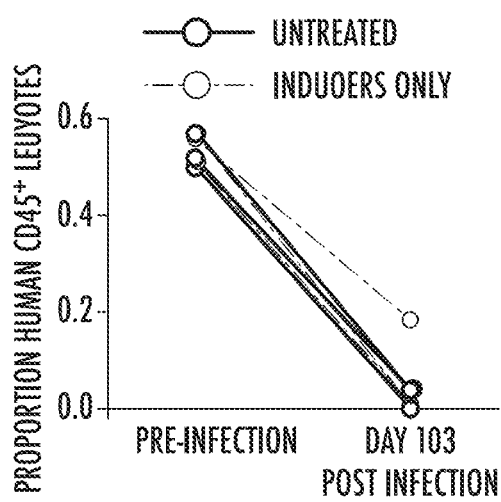
Figure 10C:
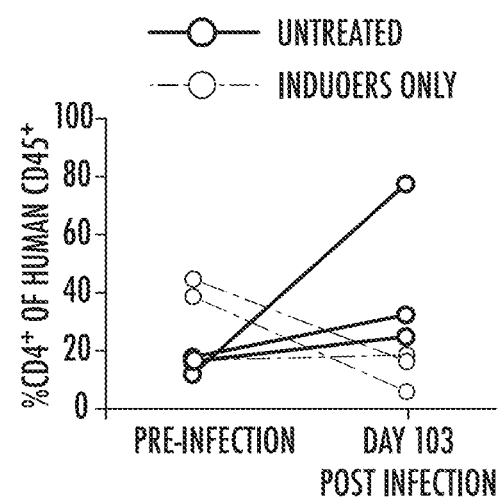

Hu-mice receiving antibodies plus vorinostat showed no significant differences in viral rebound compared to hu-mice receiving antibody alone (FIGS. 3B, 3C and 8). The same result was seen for hu-mice treated with antibodies plus I-BET151 or αCTLA4 (FIGS. 3D, 3E and 8). All 10 mice that received antibody therapy plus vorinostat showed viral rebound when the antibody dropped below therapeutic levels. Of 12 mice that received antibody therapy plus I-BET151, 11 had viral rebound, and 10 of 11 mice that received antibody plus αCTLA4 showed viral rebound. In total, of 33 mice that received antibody plus a single inducer, 31 showed viral rebound. In comparison, of 25 mice that received antibody therapy alone, 22 rebounded after the level of passively administered antibody decayed below the therapeutic threshold (p=0.64).

Of the three inducers tested, vorinostat is the only one that has also been studied in HIV-1 infected humans. Treatment with vorinostat plus ART resulted in a transient increase in resting CD4$^+$ T cell-associated HIV-1 RNA, but no change in plasma viremia, or the frequency of replication-competent HIV-1 within resting CD4$^+$ T cells (Archin et al., Nature, 2012. 487(7408): p. 482-5 and Archin et al., J. Infect. Dis. 2014. p. 1-26). The above results in hu-mice are consistent with these findings, and extend them to additional candidate inducers, demonstrating that administration of a single inducer has no significant effect on the ability of the latent reservoir to produce rebound viremia.

Example 5 Combination Therapy with Multiple Inducers

In this example, assays were carried out to determine whether a combination of inducers might be more effective than a single inducer. More specifically, all three inducers mentioned above were administered simultaneously.

Figure 4B:
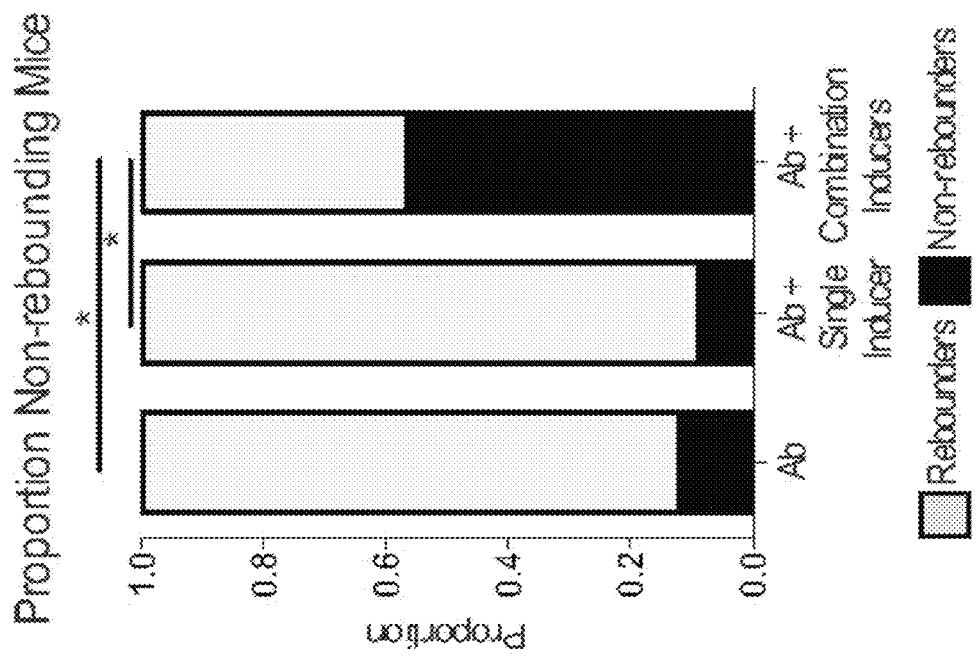
FIG. 4A and FIG. 4B are a set of diagrams showing that combination inducers decrease the incidence of rebound viremia.
Figure 4A:
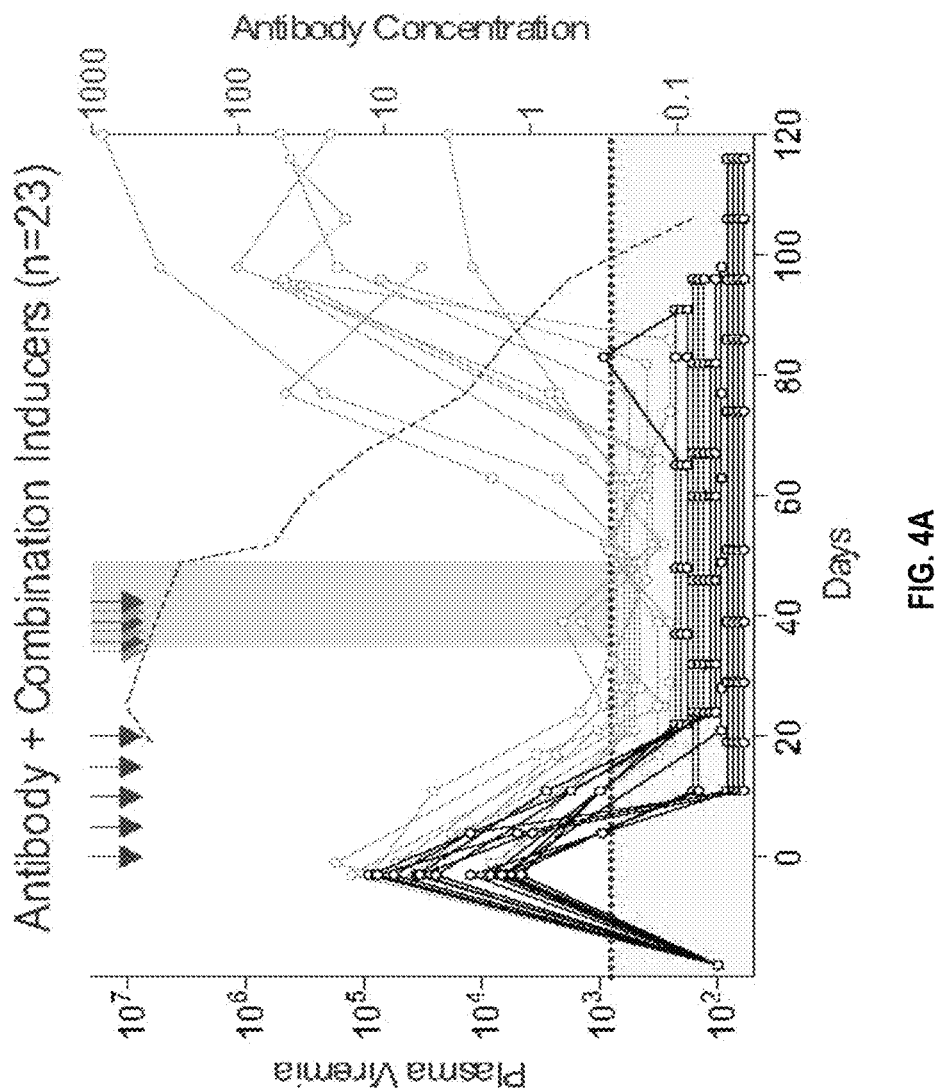

It was found that, in the absence of antibody therapy, the combination of all three inducers was not measurably toxic and did not abort or noticeably alter active infection (FIG. 6). 23 mice that initially suppressed viremia on antibody therapy were treated with the inducer combination and followed for 62-105 days after the last antibody injection (FIG. 4A). Only 10 of the 23 showed viral rebound, and the remaining 57% of the mice failed to rebound, a significant decrease in rebound frequency compared to antibody alone (p=0.0018), or antibody plus single inducers (p=0.0001) (FIG. 4B).

Importantly, when compared to antibody alone, neither single inducer nor combination inducers measurably altered the frequency of CD4$^+$ T cells remaining at the end of the experiment (FIG. 5A). Additionally, spleen T-cell associated viral RNA reflected plasma viral RNA levels at the time the experiment was terminated in that it was largely undetectable in mice that failed to rebound (FIG. 5B).

Finally, when compared to controls, hu-mice that failed to rebound after combination antibody and inducer therapy showed similar initial plasma viremias to mice that rebounded across all experimental groups (FIG. 5C). Therefore, neither initial viremia levels, nor CD4$^+$ T cell levels can account for the differences between the experimental groups.

To determine if antibody persistence or premature termination accounted for differing viral rebound outcomes, antibody levels at the time of rebound and at the terminal point were calculated. The average plasma antibody concentration at the time of viral rebound in the 59 rebounding mice was 2.97 µg/ml (FIG. 5D). Since the antibody concentrations decayed to 2.97 µg/ml at different rates in individual mice, the number of days that elapsed from when each individual mouse's antibody levels reached 2.97 µg/ml to when the mouse showed rebound viremia were calculated. 50 of 59 mice rebounded within 10 days (FIG. 5E). Of the 18 non-rebounding mice, the average antibody concentration at the terminal point was 0.44 µg/ml, with 15 out of 18 mice having antibody concentrations less than 2.97 µg/ml. Furthermore, in non-rebounding mice, an average of 20.2 days elapsed from the time antibody concentrations reached 2.97 µg/ml to termination (FIG. 5F). Thus, failure to rebound cannot be explained by antibody persistence or premature termination.

Finally, inventors could not detect viral DNA at the terminal point in the majority of mice that did not rebound, whereas the majority of mice that did rebound had detectable HIV-1 DNA, with an average of 0.09 copies per T cell (FIG. 5G). This suggests that combining vorinostat, I-BET151 and αCTLA4 with immunotherapy decreases rebound viremia in hu-mice.

In the above example, hu-mice resembled infected humans in that they contain human cells that are infected with authentic HIV-1 (Hatziioannou et al., Nat Rev Microbiol, 2012. 10(12): p. 852-67 and Brehm et al., J Infect Dis, 2013. 208 Suppl 2: p. S125-30). In addition, the kinetics of viral rebound in hu-mice after suppression of viremia with ART resembles infected humans (Horwitz et al., Proc Natl Acad Sci USA, 2013. 110(41): p. 16538-43 and Nischang et al., *PLoS ONE* 2012. p. e38853). The macaque model is valuable because it represents an immunologically intact host that may also harbor reservoirs not found in the mice. However, the infection in macaques involves non-human primate cells and SHIV or SIV, both of which differ significantly from HIV-1. While neither of the two model systems is entirely faithful, they have produced very similar results in both therapy and prevention experiments to date (West et al., Cell, 2014. 156(4): p. 633-48).

One of the strategies proposed to eliminate latent viruses involves inducing their expression under the cover of ART. In theory, this would kill infected cells while preventing the spread of infection (Deeks, S. G., Nature, 2012. 487(7408): p. 439-40). In vitro experiments indicate that silent proviruses can in fact be induced to become active (Ho et al., Cell, 2013. 155(3): p. 540-51 and Bullen et al., *Nature,* 2014, p. 1-6), but neither infected neither humans nor hu-mice show a measurable change in the reservoir after therapy with a single inducer and ART (Archin et al., *J. Infect. Dis.* 2014. p. 1-26) or bNAbs. The results here establish the principle that only a combination of inducers and bNAbs can have a significant impact on the viral reservoir in vivo.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

---

What is claimed is:

1. A kit for decreasing the size of a latent reservoir of HIV infected cells in a subject in need thereof consisting essentially of (i) antibodies 3BNC117, 10-1074, and PG16 and (ii) vorinostat, I-BET151, and αCTLA4.

* * * * *